| United States Patent [19] | [11] | 4,193,999 |
|---|---|---|
| Kraska | [45] | Mar. 18, 1980 |

[54] ANTIVIRAL AMINE DERIVATIVES OF PROPANEDIOLS

[75] Inventor: Allen R. Kraska, East Lyme, Conn.

[73] Assignee: Pfizer Inc., New York, N.Y.

[21] Appl. No.: 12,346

[22] Filed: Feb. 15, 1979

Related U.S. Application Data

[62] Division of Ser. No. 825,535, Aug. 18, 1977.

[51] Int. Cl.$^2$ .................. C07D 211/26; A61K 31/445
[52] U.S. Cl. ..................................... 424/267; 546/232
[58] Field of Search ......................... 546/232; 424/267

*Primary Examiner*—Norma S. Milestone
*Attorney, Agent, or Firm*—Connolly and Hutz

[57] ABSTRACT

Novel amine and amidine derivatives of di-O-(n-higher alkyl and alkenyl)-glycerols and -propanediols, and their pharmaceutically acceptable acid addition salts, are useful for combating viral infections in mammals. Of particular interest is 1,3-di-O-(n-hexadecyl)-2-O-(3-aminopropyl)-glycerol, and its pharmaceutically acceptable acid addition salts.

9 Claims, No Drawings

ANTIVIRAL AMINE DERIVATIVES OF PROPANEDIOLS

CROSS-REFERENCE TO RELATED APPLICATION

This application is a division of application Ser. No. 825,535 filed Aug. 18, 1977.

BACKGROUND OF THE INVENTION

Virus infections which attack mammals, including man, are normally contagious afflictions which are capable of causing great human suffering and economic loss. Unfortunately, the discovery of antiviral compounds is far more complicated and difficult than the discovery of antibacterial and antifungal agents. This is due, in part, to the close structural similarity of viruses and the structure of certain essential cellular components such as ribonucleic and deoxyribonucleic acids. Nevertheless, numerous non-viral "antiviral agents", i.e. substances "which can produce either a protective or therapeutic effect to the clear detectable advantage of the virus infected host, or any material that can significantly enhance antibody formation, improve antibody activity improve non-specific resistance, speed convalescence or depress symptoms" [Herrman et al., *Proc. Soc. Exptl. Biol. Med.*, 103, 625 (1960)], have been described in the literature. The list of reported antiviral agents includes, to name a few, interferon and synthetic materials such as amantadine hydrochloride, pyrimidines, biguanides, guanidine, pteridines and methisazone. Because of the rather narrow range of viral infections that can be treated by each of the antiviral agents commercially available at the present time, new synthetic antiviral agents are always welcomed as potentially valuable additions to the armamentarium of medical technology.

The cells of mammals produce, in response to virus infection, a substance which enables cells to resist the multiplication of a variety of viruses. The viral-resisting or viral-interfering substances are referred to as "interferons". The interferons are glycoproteins which may differ in their physico-chemical properties, but all exhibit the same biological properties; namely, they inhibit a wide range of unrelated viruses, have no toxic or other deleterious effects on cells, and are species-specific (Lockart, Frontiers of Biology, Vol. 2, "Interferons", edited by Finter, W. B. Saunders Co., Philadephia, 1966, pages 19–20).

No practical, economical method has yet been developed for the preparation of exogenous interferon for routine clinical use against viral infections. An alternative approach to producing interferon has, therefore, been pursued, which comprises administering to the animal to be protected or treated a non-viral substance which stimulates—or induces—production of interferon in the cells. The interferon produced in this fashion is referred to as "endogenous" interferon.

U.S. Pat. No. 2,738,351 discloses that compounds of the general formula

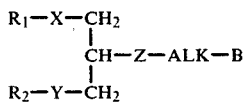

wherein each of $R_1$ and $R_2$ may be alkyl, aralkyl, aryl, cycloalkyl, nitro-substituted aryl, halogen-substituted aryl, alkyl-substituted aryl, or alkoxy-substituted aryl, each of X, Y and Z may be oxygen, sulfur or sulfonyl, ALK is straight or branched alkylene of from one to six carbon atoms, and B may be di(lower)alkylamino, piperidino, morpholino, pyrrolidino, (lower alkyl)pyrrolidino, N'-alkyl-piperazino or pipecolino, are local anesthetic agents. Additionally, the discussion of alternate synthetic routes (see Col. 1, ll. 57–70, of said patent) discloses intermediates of the above formula wherein B is amino and (lower alkyl)amino. However, none of the compounds specifically enumerate in the disclosure of said patent contain an alkyl $R_1$ or $R_2$ larger than n-pentyl. Furthermore, in none of these compounds are both $R_1$ and $R_2$ alkyl and both X and Y oxygen.

Insecticidal and miticidal compounds of the formula

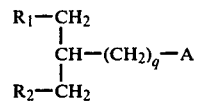

wherein $R_1$ and $R_2$ may each be, inter alia, lower alkylthio; q is 0 to 5; and A may be, inter alia, 1-piperidino or di(lower alkyl)amino are disclosed in Japanese Pat. No. J7-6042-177.

SUMMARY OF THE INVENTION

It has now been discovered that certain novel amine and amidine derivatives of di-O-(n-higher alkyl and alkenyl)-glycerols and -propanediols are capable of combating viral infections in mammals. The novel compounds of this invention have the formulae

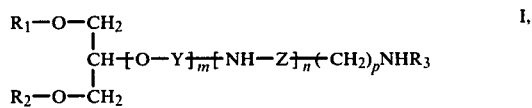

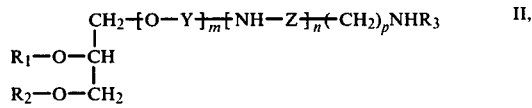

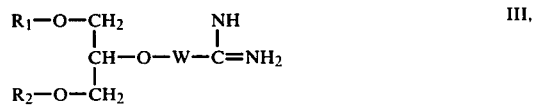

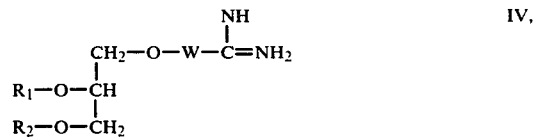

and

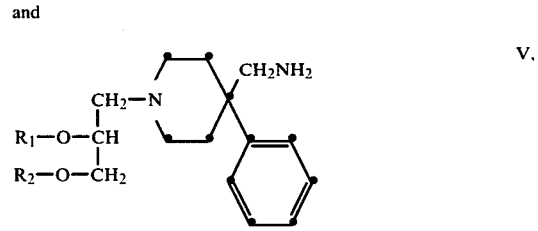

and the pharmaceutically acceptable acid addition salts thereof, wherein $R_1$ and $R_2$ are each selected from the group consisting of normal alkyl of from 12 to 20 carbon atoms and normal alkenyl not having a double bond in the 1-position of from 12 to 20 carbon atoms, Y is selected from the group consisting of alkylene of from 2 to 4 carbon atoms, the two valencies being on different carbon atoms;

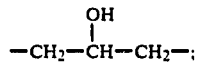

ortho-, meta- and para-phenylenedimethylene;

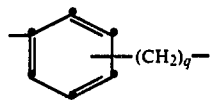

wherein q is an integer of from one to three, and the left bond is connected to O; and

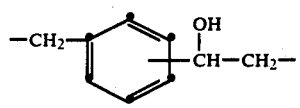

wherein the left bond is connected to O,

Z is selected from the group consisting of alkylene of from 2 to 4 carbon atoms, the two valencies being on different carbon atoms; ortho-, meta- and para-phenylenedimethylene;

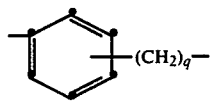

wherein q is an integer of from one to three and the $-(CH_2)_q-$ group is connected to $-(CH_2)_p NHR_3$; an

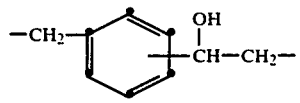

wherein the

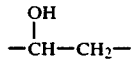

group is connected to $-(CH_2)_p NHR_3$, $R_3$ is selected from the group consisting of hydrogen, alkyl of from 2 to 4 carbon atoms and ω-hydroxy(normal alkyl) of from 2 to 4 carbon atoms, m, n and p are each 0 or 1, the sum of m, n and p being 0 or 1, $R_3$ being hydrogen when m is 0, and $R_3$ being other than ω-hydroxy(normal alkyl) when m is 1 and Y is

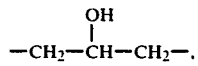

W is selected from the group consisting of alkylene of from 1 to 4 carbon atoms, the two valencies being on different carbon atoms when W is other than methylene; ortho-, meta- and para-phenylene; and

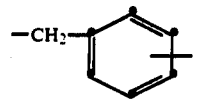

wherein the left bond is connected to O.

The invention disclosed herein comprises the novel antiviral compounds of formulae I to V, the novel pharmaceutical compositions containing an antivirally effective amount of a compound of formulae I to V as the essential active ingredient in a pharmaceutically acceptable carrier, the novel method of prophylactically controlling a viral infection in a mammal which comprises administering an amount effective to prophylactically control said viral infection of a compound of formulae I to V, and the novel method of inducing the production of interferon in a mammal which comprises administering an amount effective to induce the productio of interferon of a compound of formulae I to V.

DETAILED DESCRIPTION OF THE INVENTION

The compounds of this invention exhibit antiviral activity against a wide variety of viruses in vivo in mammals and in vitro in mammalian tissue culture. At least a substantial portion of this activity results from the ability of said compounds to induce the production of interferon in the cells, i.e. endogenous interferon.

By "pharmaceutically acceptable" acid addition salts is meant those salts which are non-toxic at the dosages administered. The pharmaceutically acceptable acid addition salts which may be employed include such water-soluble and water-insoluble salts as the hydrochloride, hydrobromide, phosphate, nitrate, sulfate, acetate, hexafluorophosphate, citrate, gluconate, benzoate, propionate, butyrate, sulfosalicylate, maleate, laurate, malate, fumarate, succinate, oxalate, tartrate, amsonate (4,4'-diaminostilbene-2,2'-disulfonate), pamoate (1,1'-methylene-bis-2-hydroxy-3-naphthoate), stearate, 3-hydroxy-2-naphthoate, p-toluenesulfonate, methanesulfonate, lactate, and suramin salts.

One preferred group of the compounds of formulae I–V consists of the hydrochloride salts of the bases of formulae I–V.

Another preferred group of the compounds of formulae I–V consists of those wherein $R_1$ and $R_2$ are each normal alkyl of from 14 to 18 carbon atoms.

Another preferred group of the compounds of formulae I–V consists of those wherein $R_1$ and $R_2$ are each normal alkyl of from 14 to 18 carbon atoms and contain the same number of carbon atoms.

Another preferred group of the compounds of formulae I–V consists of those wherein $R_1$ and $R_2$ are each n-hexadecyl.

Another preferred group of the compounds of this invention consists of those of formula I.

Another preferred group of the compounds of this invention consists of those of formula II.

Another preferred group of the compounds of this invention consists of those of formula V.

One preferred group of the compounds of formulae I and II consists of those wherein m is 1, n is 0, p is 0, and $R_3$ is hydrogen.

Another preferred group of the compounds of formulae I and II consists of those wherein m is 1, n is 0, p is 0, R$_3$ is hydrogen, and Y is straight chain alkylene of from 2 to 4 carbon atoms.

Another preferred group of the compounds of formulae I and II consists of those wherein m is 1, n is 0, p is 0, R$_3$ is hydrogen, and Y is ortho-, meta- or para-phenylenedimethylene.

Particularly valuable are the following compounds and their pharmaceutically acceptable acid addition salts:

1,3-di-O-(n-hexadecyl)-2-O-(3-aminopropyl)-glycerol,
1,2-di-O-(n-hexadecyl)-3-O-(3-aminopropyl)-glycerol,
1,3-di-O-(n-hexadecyl)-2-O-(meta-aminomethylbenzyl)-glycerol,
1,2-di-O-(n-hexadecyl)-3-O-(meta-aminomethylbenzyl)-glycerol,
1,2-di-O-(n-tetradecyl)-3-O-(meta-aminomethylbenzyl)-glycerol
1,3-di-O-(n-hexadecyl)-2-O-(meta-aminomethylphenyl)-glycerol,
1,3-di-O-(n-hexadecyl)-2-O-(para-aminomethylphenyl)-glycerol,
1,2-di-O-(n-hexadecyl)-3-O-(para-aminomethylphenyl)-glycerol,
1,2-di(n-hexadecyloxy)-3-(meta-aminomethylbenzylamino)-propane,
1,2-di(n-hexadecyloxy)-3-aminomethyl-propane,
1,2-di-O-(n-hexadecyl)-3-O-(meta-amidinobenzyl)-glycerol,
1-[2,3-di(n-octadecyloxy)propyl]-4-aminomethyl-4-phenylpiperidine,
1-[2,3-di(n-hexadecyloxy)propyl]-4-aminomethyl-4-phenylpiperidine, and
1-[2,3-di(n-tetradecyloxy)propyl]-4-aminomethyl-4-phenylpiperidine.

The compounds of formulae I and II above may be prepared from the appropriate 1,2-di-O-(n-higher alkyl or alkenyl)-glycerol and 1,3-di-O-(n-higher alkyl or alkenyl)-glycerol starting materials by methods familiar to those skilled in the art. For example:

(a) those compounds wherein m is 1, R$_3$ is H and Y is 3-propylene may be prepared by condensing the starting material with acrylonitrile in aqueous solution under strongly basic conditions to form the 2-cyanoethyl derivative, which is then hydrogenated;

(b) those compounds wherein m is 1, R$_3$ is H and Y is 2-ethylene may be prepared by reacting the 2-cyanoethyl derivative of the starting material with formic acid under strongly acidic conditions to form the 2-carboxyethyl derivative, which is then reacted under strongly acidic conditions with hydrazoic acid;

(c) those compounds wherein m is 1, R$_3$ is H and Y is 4-butylene may be prepared by adding an allyl radical to the starting material by reacting it with an allyl halide under strongly basic conditions, hydroborating the allyl derivative, oxidizing the resulting intermediate with hydrogen peroxide in basic aqueous solution to the 3-hydroxypropyl derivative, reacting the 3-hydroxypropyl derivative with a sulfonyl chloride RSO$_2$Cl (e.g. p-toluenesulfonyl chloride) under basic conditions to form the corresponding sulfonate ester (e.g. the tosylate), substituting a cyano group for the RSO$_3$— group by reaction with sodium cyanide, and then reducing the resulting 3-cyanopropyl derivative;

(d) those compounds wherein m is 1, R$_3$ is H and Y is 2-propylene may be prepared by following procedure (c) through the hydrogen peroxide oxidation step, isolating the 2-hydroxypropyl oxidation side product, and then subjecting the 2-hydroxypropyl derivative to the remainder of procedure (c) using sodium azide in place of sodium cyanide;

(e) those compounds wherein m is 1, R$_3$ is H and Y is 2-hydroxy-3-propylene may be prepared by oxidizing the allyl derivative of the starting material with a percarboxylic acid (e.g. m-chloroperbenzoic acid) to the 2,3-epoxypropyl derivative, and reacting the latter with sodium azide to form the 3-azido-2-hydroxypropyl derivative, which is then reduced;

(f) those compounds wherein m is 1, R$_3$ is H and Y is phenylenedimethylene may be prepared by reacting the starting material with a cyanobenzyl halide under strongly basic conditions, and then reducing the resulting cyanobenzyl derivative with a hydride reagent such as lithium aluminum hydride;

(g) those compounds wherein m is 1, R$_3$ is H, Y is

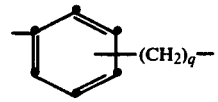

and q is an integer of from one to three may be prepared by reacting the starting material with a sulfonyl chloride RSO$_2$Cl (e.g. p-toluenesulfonyl chloride) under basic conditions to form the corresponding sulfonate ester (e.g. the tosylate) of di-O-(n-higher alkyl or alkenyl)-glycerol, substituting a cyanophenoxy or ω-cyanoalkylphenoxy group for the RSO$_3$— group by reaction with e.g. sodium cyanophenolate and then hydrogenating the resulting cyanophenyl or cyanoalkylphenyl derivative of the di-O-(n-higher alkyl or alkenyl)-glycerol starting material;

(h) those compounds wherein m is 1, R$_3$ is normal alkyl and Y is other than

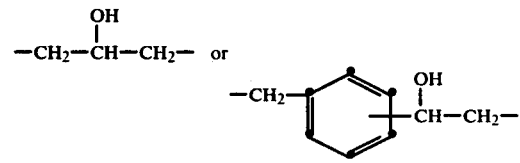

may be prepared by acylating the corresponding compound wherein R$_3$ is H with an acyl halide under basic conditions, and then reducing the resulting N-acyl derivative;

(i) those compounds wherein m is 1, R$_3$ is isopropyl and Y is other than

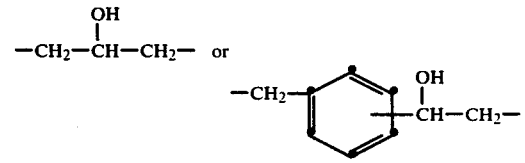

may be prepared by reacting the corresponding compound wherein R$_3$ is H with acetone under acidic conditions and hydrogenating the resulting imine (e.g. with sodium borohydride);

(j) those compounds wherein m is 1, R$_3$ is other than H and Y is 2-ethylene may be prepared by oxidizing the allyl derivative of the di-O-(n-higher alkyl or alkenyl)-glycerol starting material by sequential treatment in the presence of water with osmium tetroxide (or potassium permanganate) and sodium periodate to the formylmethyl derivative, reacting the formylmethyl derivative with the amine R$_3$NH$_2$ under acidic conditions, and hydrogenating the N-alkylidene or N-hydroxyalkylidene product;

(k) those compounds wherein m is 1, R$_3$ is alkyl and Y is

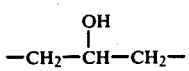

may be prepared by reacting the 2,3-epoxypropyl derivative of the starting material with the amine R$_3$NH$_2$;

(l) those compounds wherein p is 1 may be prepared by reacting a sulfonate ester (e.g. the tosylate) of the appropriate di-O-(n-higher alkyl or alkenyl)-glycerol [prepared from the starting material as in (g)] with sodium cyanide, and then hydrogenating the resulting cyano derivative of di(n-higher alkyloxy or alkenyloxy)propane;

(m) those compounds wherein m, n and p are all 0 may be prepared as in (l) using sodium azide in place of sodium cyanide;

(n) those compounds wherein n is 1 and Z is 3-propylene may be prepared by condensing the corresponding compound wherein m, n and p are all 0 with acrylonitrile in aqueous solution under strongly basic conditions to form the N-(2-cyanoethyl)-amino derivative of di(n-higher alkyloxy or alkenyloxy)propane, which is then hydrogenated;

(o) those compounds wherein n is 1 and Z is phenylenedimethylene may be prepared by reacting a xylylenediamine with a sulfonate ester (e.g. the tosylate) of the appropriate di-O-(n-higher alkyl or alkenyl)-glycerol; and (p) those compounds wherein m is 1, R$_3$ is alkyl and Y is

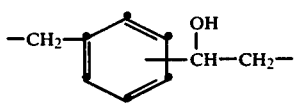

may be prepared by reducing a cyanobenzyl derivative of the di-O-(n-higher alkyl or alkenyl)-glycerol starting material to the formylbenzyl derivative, reducing the formylbenzyl derivative in the presence of trimethylsulfonium iodide to the 1,2-epoxyethylbenzyl derivative, and then reacting the latter derivative with the amine R$_3$NH$_2$.

The skilled worker in the art will realize that additional compounds of formulae I and II may be prepared by using obvious variations of the methods of synthesis outlined above.

The compounds of formulae III and IV above may also be prepare from the appropriate 1,2-di-O-(n-higher alkyl or alkenyl)-glycerol and 1,3-di-O-(n-higher alkyl or alkenyl)-glycerol starting material by methods familiar to those skilled in the art. For example, those compounds wherein W is phenylene may be prepared by condensing a cyanophenyl derivative of the starting material with ethanol or ethanethiol in a hydrogen chloride saturated inert solvent such as dioxane to form the corresponding ethylbenzimidate or ethylthiobenzimidate hydrochloride, followed by nucleophilic substitution with ammonia and elimination of ethanol or ethanethiol which is carried out in ammonia saturated ethanol. Those compounds wherein W is

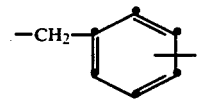

may be prepared in like manner from a cyanobenzyl derivative of the starting material. Those compounds where W is alkylene may be prepared in like manner from the appropriate cyano (lower alkyl) derivative of the starting material. When W is methylene, said derivative may be prepared by reacting the starting material with chloro-, bromo-, or iodoacetonitrile.

The compounds of formula V above may be prepared from the appropriate 1,2-di-O-(n-higher alkyl or alkenyl)-glycerol starting materials by methods familiar to those skilled in the art. For example, the tosyl derivative of the starting material may be reacted with 4-cyano-4-phenylpiperidine hydrochloride, and the resulting compound then reduced.

Acid addition salts of the bases of formulae I–V may be prepared by conventional procedures such as by mixing the amine or amidine compound in a suitable solvent with the required acid and recovering the salt by evaporation or by precipitation upon adding a non-solvent for the salt. Hydrochloride salts may readily be prepared by passing hydrogen chloride through a solution of the amine or amidine compound in an organic solvent. As can be seen by reference to the examples herein, many of the isolated hydrochloride or dihydrochloride salts of the bases of formulae I–V tend to contain a significant water content. Whether this observed "trapped" water is randomly occluded during crystallization, or corresponds to formation of true molecular hydrates, or results from the occurrence of some other phenomenon, is not known. In any event, the salts containing "trapped" water may be efficaciously formulated and administered without preliminary dehydration.

The 1,2-di-O-(n-higher alkyl)-glycerol starting materials may be prepared by the method of Kates, M. et al., *Biochemistry*, 2, 394 (1963). The 1,3-di-O-(n-higher alkyl)-glycerol starting materials may be prepared by the method of Damico, R., et al., *J. Lipid Res.*, 8, 63 (1967). The 1,2- and 1,3-di-O-(n-higher alkenyl)-glycerol starting materials may be prepared by the method of Bauman, W. J. and Mangold, H. K., *J. Org. Chem.*, 31, 498 (1966).

The antiviral activity of the compounds of this invention was determined by the use of two independent procedures. In the first, the test compound is administered to mice by the intraperitoneal route eighteen to twenty-four hours prior to challenging them with a lethal dose of encephalomyocarditis (EMC) virus. Survival data are taken during the ten days after challenge and compared with the data for unprotected animals. The procedure in which the drug is given eighteen to twenty-four hours before, and at a distinctly different site from, virus injection is designed to eliminate local effects between drug and virus and identify only those compounds which produce a systemic antiviral response.

In the second procedure, monolayers of human nasal polyp cells grown on microtiter plates are treated with the test compound about eighteen hours before treatment with a lethal dose of vesicular stomatitis virus (VSV). The test compound is washed away from the monolayers before virus treatment. Culture fluid extracted from the plates after a post challenge incubation period is titrated for the amount of infectious virus present in microtiter plates of L-929 mouse fibroblasts. Comparison is made with the virus yield data for culture fluid extracted from unprotected polyp cells.

Additionally, many of the compounds of this invention were tested for their ability to enhance the known antiviral activity of polyinosinic:polycytidylic acid. Finally, certain of the compounds were also tested for their ability to induce circulating interferon in mice after parenteral administration, using the procedure described by Hoffman, W. W., et al., *Antimicrobial Agents and Chemotherapy*, 3, 498–501 (1973).

Parenteral, topical or intranasal administration of the above-described amines and amidines to a mammal before exposure of the mammal to an infectious virus provides rapid resistance to the virus. Preferably, administration should take place from about two days to about one day before exposure to the virus, although this will vary somewhat with the particular animal species and the particular infectious virus.

When the materials of this invention are administered, they are most easily and economicaly used in a dispersed form in an acceptable carrier. When it is said that this material is dispersed, it means that the particles may be molecular in size and held in true solution in a suitable solvent or that the particles may be colloidal in size and dispersed through a liquid phase in the form of a suspension or an emulsion. The term "dispersed" also means that the particles may be mixed with and spread throughout a solid carrier so that the mixture is in the form of a powder or dust. This term is also meant to encompass mixtures which are suitable for use as sprays, including solutions, suspensions or emulsions of the agents of this invention.

When administered parenterally (subcutaneously, intramuscularly, intraperitoneally) the materials of this invention are used at a level of from about 1 mg./kg. of body weight to about 250 mg./kg. body weight. The favored range is from about 5 mg./kg. to about 100 mg./kg. of body weight, and the preferred range from about 5 mg. to about 50 mg./kg. of body weight. The dosage, of course, is dependent upon the mammal being treated and the particular amine or amidine compound involved and is to be determined by the individual responsible for its administration. Generally, small doses will be administered initially with gradual increase in dosage until the optimal dosage level is determined for the particular subject under treatment.

Vehicles suitable for parenteral injection may be either aqueous such as water, isotonic saline, isotonic dextrose, Ringer's solution, or non-aqueous such as fatty oils of vegetable origin (cottonseed, peanut oil, corn, sesame) and other non-aqueous vehicles which will not interfere with the efficacy of the preparation and are non-toxic in the volume or proportion used (glycerol, ethanol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol.

In practicing the intranasal route of administration of this invention any practical method can be used to contact the antiviral agent with the respiratory tract of the mammal. Effective methods include administration of the agent by intranasal or nasopharyngeal drops and by inhalation as delivered by a nebulizer or an aerosol. Such methods of administration are of practical importance because they provide an easy, safe and efficient method of practicing this invention. For intranasal administration of the agent, usually in an acceptable carrier, a concentration of agent between 1.0 mg./ml. and 100 mg./ml. is satisfactory. Concentrations in the range of about 30 to 50 mg./ml. allow administration of a convenient volume of material.

For topical application the antiviral agents are most conveniently used in an acceptable carrier to permit ease and control of application and better absorption. Here also concentrations in the range of from about 1.0 mg./ml. to about 250 mg./ml. are satisfactory. In general, in the above two methods of administration a dose within the range of about 1.0 mg./kg. to about 250 mg./kg. of body weight and, preferably, from about 5.0 mg./kg. to about 50 mg./kg. of body weight will be administered.

The compounds employed in this invention may be employed alone, i.e., without other medicinals, as mixtures of more than one of the herein-described compounds, or in combination with other medicinal agents, such as analgesics, anesthetics, antiseptics, decongestants, antbiotics, vaccines, buffering agents and inorganic salts, to afford desirable pharmacological properties. Further, they may be administered in combination with hyaluronidase to avoid or, at least, to minimize local irritation and to increase the rate of absorption of the compound. Hyaluronidase levels of at least about 150 (U.S.P.) units are effective in this respect although higher or lower levels can, of course, be used.

Those materials of this invention which are water-insoluble, including those which are of low and/or difficult solubility in water, are, for optimum results, administered in formulations, e.g., suspensions, emulsions, which permit formation of particle sizes of less than about $20\mu$. The particle sizes of the formulations influence their biological activity apparently through better absorption of the active materials. In formulating these materials various surface active agents and protective colloids are used. Suitable surface active agents are the partial esters of common fatty acids, such as lauric, oleic, stearic, with hexitol anhydrides derived from sorbitol, and the polyoxyethylene derivatives of such ester products. Such products are sold under the trademarks "Spans" and "Tweens," respectively, and are available from ICI United States Inc., Wilmington, Del. Cellulose ethers, especially cellulose methyl ether (Methocel, available from the Dow Chemical Co., Midland, Mich.) are highly efficient as protective colloids for use in emulsions containing the materials of this invention.

The water-soluble materials described herein are administered for optimum results in aqueous solution. Typically they are administered in phosphate buffered saline. The water-insoluble compounds are administered in formulations of the type described above or in various other formulations as previously noted. Dimethylsulfoxide serves as a suitable vehicle for water-insoluble compounds. A representative formulation for such compounds comprises formulating 25 to 100 mg. of the chosen drug as an emulsion by melting and mixing with equal parts of polysorbate 80 and glycerin to which hot (80° C.) water is added under vigorous mixing. Sodium chloride is added in a concentration solution to a final concentration of 0.14 M and sodium phosphate, pH 7, is added to a final concentration of 0.01 M to give, for example, the following representative composition:

|  | mg./ml. |
| --- | --- |
| Drug | 50.0 |
| Polysorbate 80 | 50.0 |
| Glycerin | 50.0 |
| Sodium Phosphate Monobasic Hydrous | 1.4 |
| Sodium Chloride | 7.9 |
| Water | 842.0 |
|  | 1001.3 |

In certain instances, as where clumping of the drug particles occurs, sonication is employed to provide a homogenous system.

The following examples illustrate the invention but are not to be construed as limiting the same.

EXAMPLE 1

1,3-Di-O-(n-hexadecyl)-2-O-(3-aminopropyl)-glycerol Hydrochloride

A. 1,3-Di-O-(n-hexadecyl)-2-O-(2-cyanoethyl)-glycerol

A mixture of 1,3-di-O-(n-hexadecyl)-glycerol (80 g., 148 mmoles), acrylonitrile (1.49 kg., 28.1 moles) and aqueous 2 N sodium hydroxide (1.2 l.) was heated to 50° C. Tetrabutylammonium hydroxide (19.2 g. of 40 wt. % aqueous solution, 29.15 mmoles) was slowly added, causing the temperature of the exothermic reaction mixture to rise to about 80° to 90° C. The reaction mixture was then stirred for 20 minutes without any external heating, followed by cooling to 20° C. and addition of water (1.0 l.). A solid material, a mixture of unreacted and cyanoethylated 1,3-di-O-(n-hexadecyl)-glycerol, was isolated and treated again with fresh acrylonitrile (1.49 kg., 28.1 moles), aqueous 2 N sodium hydroxide (1.2 l.) and tetrabutylammonium hydroxide (19.2 g. of 40 wt. % aqueous solution, 29.15 mmoles) for 20 minutes with stirring at 50° C., followed by cooling and addition of water (1.0 l.). The resulting 1,3-di-O-(n-hexadecyl)-2-O-(2-cyanoethyl)-glycerol solids were filtered, washed consecutively with water, methanol and acetonitrile, and dried [82 g., 93% yield, m.p. 45°-46° C., ir (CHCl$_3$) 2250 cm$^{-1}$, n.m.r. (CDCl$_3$) $\delta$ 3.92 (t, 2, NCC$\underline{H}_2$CH$_2$O—), 3.33–3.67 (m, 9, —OC$\underline{H}$[C$\underline{H}_2$OC$\underline{H}_2$C$_{15}$H$_{31}$]$_2$), 2.62 (t, 2, NCC$\underline{H}_2$CH$_2$O—) and 0.75–1.58 (m, 62, aliphatic protons)].

B. Title Compound

A mixture of 1,3-di-O-(n-hexadecyl)-2-O-(2-cyanomethyl)-glycerol (20.5 g., 34.5 mmoles), tetrahydrofuran (200 ml.), ethanol (10 ml.) and Raney nickel catalyst (3 g.) was saturated with ammonia gas at 0° to 5° C. and then hydrogenated (50 psi) in a Paar hydrogenator for 3 hours at room temperature. The mixture was then filtered, the catalyst washed with tetrahydrofuran (50 ml.), and the total filtrate evaporated in vacuo to an oil. This procedure was repeated three more times with fresh reactants and catalyst to yield a total of 77 g. of oil. The oil was dissolved in ether (500 ml.) and the solution washed with 2 wt. % aqueous ammonium hydroxide solution (500 ml.), dried (MgSO$_4$), filtered and evaporated in vacuo to yield a solid. The solid was dissolved in methanol (300 ml.) and the solution saturated with hydrogen chloride gas and then evaporated in vacuo to a solid. This solid was crystallized from ethyl acetate to yield the named product with a slight impurity (63 g., 72% yield, m.p. 69°-70° C.), and then recrystallized twice from isopropanol:acetonitrile (1:1, 800 ml.) [47.5 g., 54% yield, m.p. 58°-59° C., n.m.r. (CDCl$_3$) $\delta$ 3.84 (t, 2, H$_2$NCH$_2$CH$_2$C$\underline{H}_2$O—), 3.55 (m, 9, —OC$\underline{H}$[CH$_2$OCH$_2$C$_{15}$H$_{31}$]$_2$), 3.24 (t, 2, H$_2$NC$\underline{H}_2$CH$_2$CH$_2$O—), 2.04 (m, 2, H$_2$NCH$_2$C$\underline{H}_2$CH$_2$O—) and 0.90–1.32 (m, 62, aliphatic protons), elemental analysis calculated: 72.04% C; 12.73% H; 2.21% N; found: 71.80% C; 12.41% H; 2.30% N].

EXAMPLES 2–7

In like manner to that described in Example 1 the following compounds were prepared by using the appropriate 1,3- or 1,2-di-O-(n-higher alkyl)-glycerol as starting material:

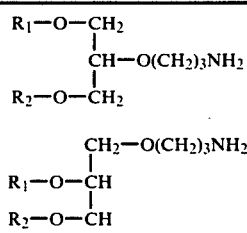

R$_1$—O—CH$_2$  
          |  
          CH—O(CH$_2$)$_3$NH$_2$    I
          |  
R$_2$—O—CH$_2$

CH$_2$—O(CH$_2$)$_3$NH$_2$   II
          |  
R$_1$—O—CH  
          |  
R$_2$—O—CH

| Example Number | Structure | R$_1$ | R$_2$ | Molecular Formula | M.P. (°C.) | Calculated (%) C | H | N | Found (%) C | H | N |
| --- | --- | --- | --- | --- | --- | --- | --- | --- | --- | --- | --- |
| 2 | I | n-dodecyl | n-dodecyl | C$_{30}$H$_{63}$O$_3$N . HCl . 3/2 H$_2$O | 76–77 | 65.60 | 12.29 | 2.54 | 65.45 | 11.91 | 2.61 |
| 3 | I | n-tetradecyl | n-tetradecyl | C$_{34}$H$_{71}$O$_3$N . HCl . H$_2$O | 57–58 | 68.47 | 12.50 | 2.35 | 68.51 | 11.24 | 2.29 |
| 4 | I | n-octadecyl | n-octadecyl | C$_{42}$H$_{87}$O$_3$N . HCl | 64–65 | 73.04 | 12.84 | 2.03 | 72.96 | 12.56 | 1.99 |
| 5 | II | n-tetradecyl | n-tetradecyl | C$_{34}$H$_{71}$O$_3$N . HCl | 90–91 | 70.60 | 12.55 | 2.42 | 70.74 | 12.85 | 2.68 |
| 6 | II | n-hexadecyl | n-hexadecyl | C$_{38}$H$_{79}$O$_3$N . HCl . ¾ H$_2$O | 76–78 | 70.54 | 12.77 | 2.16 | 70.42 | 12.17 | 2.07 |
| 7 | II | n-octadecyl | n-octadecyl | C$_{42}$H$_{87}$O$_3$N . HCl . H$_2$O | 67–69 | 71.19 | 12.80 | 1.98 | 70.95 | 12.19 | 1.91 |

EXAMPLE 8

1,3-Di-O-(n-hexadecyl)-2-O-(2-aminoethyl)-glycerol Hydrochloride

A. 1,3-di-O-(n-hexadecyl)-2-O-(2-carboxyethyl)-glycerol

A mixture of 1,3-di-O-(n-hexadecyl)-2-O-(2-cyanoethyl)-glycerol (4.8 g., 8.1 mmoles), concentrated hydrochloric acid (50 ml.) and formic acid (50 ml.) was stirred for 16 hours at reflux, then cooled and extracted with ether (3×100 ml.). The combined ether extract was washed with water (200 ml.), dried (MgSO$_4$), filtered and evaporated in vacuo to yield 1,3-di-O-(n-hexadecyl)-2-O-(2-carboxyethyl)-glycerol solids (4.5 g.), which were purified by silica gel chromatography (elution with toluene:ethanol) [3.5 g., 71% yield, m.p. 43°–45° C., ir (CHCl$_3$) 1740 cm$^{-1}$, n.m.r. (CDCl$_3$) δ 3.93 (t, J=6 Hz, 2, —OC$\underline{H}_2$CH$_2$COOH) and 2.65 (t, J=6 Hz, 2, —OCH$_2$C$\underline{H}_2$COOH)].

B. Title Compound 1,3-Di-O-(n-hexadecyl)-2-O-(2-carboxyethyl)-glycerol (3.5 g., 5.7 mmoles) was dissolved in a mixture of benzene (55 ml.) and concentrated sulfuric acid (5.89 g.). Hydrazoic acid (6.34 ml. of 4.65 wt. % benzene solution, 6.0 mmoles) was then added dropwise and the resulting mixture stirred for 2 hours at room temperature. Thin layer chromatography (TLC) analysis showed about 50% reaction of the 2-carboxyethyl compound. Additional hydrazoic acid (6.34 ml. of 4.65 wt. % benzene solution, 6.0 mmoles) was added dropwise and the reaction mixture stirred for another 16 hours at 40° C. TLC analysis now showed that the reaction was essentially complete. Water (50 ml.) and aqueous 2 N sodium hydroxide were then added and the resulting mixture extracted with ether (3×200 ml.). The combined ether extract was dried (Na$_2$SO$_4$), filtered, saturated with hydrogen chloride gas and evaporated in vacuo to yield a solid. The solid was purified by silica gel chromatography (elution with chloroform:methanol) and recrystallized from hot ethyl acetate [570 mg., 16% yield, m.p. 79°–80° C., n.m.r. (CDCl$_3$) δ 3.95 (m, 2, —OC$\underline{H}_2$CH$_2$NH$_2$) and 3.22 (m, 2, —OCH$_2$C$\underline{H}_2$NH$_2$), elemental analysis calculated: 71.62% C; 12.67% H; 2.26% N; found: 70.90% C; 12.19% H; 2.05% N].

EXAMPLE 9

1,3-Di-O-(n-hexadecyl)-2-O-(3-ethylaminopropyl)-glycerol Hydrochloride

A. 1,3-Di-O-(n-hexadecyl)-2-O-(3-acetamidopropyl)-glycerol 1,3-Di-O-(n-hexadecyl)-2-O-(3-aminopropyl)-glycerol hydrochloride (1.0 g., 1.6 mmoles) was added to a mixture of potassium carbonate (830 mg., 6.0 mmoles) and benzene (75 ml.). Acetyl chloride (150 mg., 1.9 mmoles) was then added and the resulting mixture stirred for one hour at reflux. Additional acetyl chloride (150 mg., 1.9 moles) was added and the reaction mixture stirred for another hour at reflux. TLC analysis showed that the reaction was essentially complete. The reaction mixture was cooled, water (75 ml.) added, and the resulting mixture extracted with ether (3×100 ml.). The combined ether extract was dried (MgSO$_4$), filtered and evaporated in vacuo to yield the named compound [800 mg., 79% yield, m.p. 53°–54° C., ir (CHCl$_3$) 3400 and 1670 cm$^{-1}$, n.m.r. (CDCl$_3$) δ 1.97 (s, 3, —NHCOC$\underline{H}_3$)].

B. Title Compound 1,3-Di-O-(n-hexadecyl)-2-O-(3-acetamidopropyl)-glycerol (700 mg., 1.1 mmoles) was dissolved in ether (100 ml.) and treated with lithium aluminum hydride (500 mg., 13 mmoles). Water (100 ml.) was then added and the mixture extracted with ether (2×100 ml.). The combined ether extract was dried (MgSO$_4$), filtered, treated with hydrogen chloride gas and evaporated in vacuo to a solid, which was recrystallized from hot ethyl acetate [470 mg., 66% yield, m.p. 61°–62° C., n.m.r. (CDCl$_3$) δ 1.47 (t, 3, —NHCH$_2$C$\underline{H}_3$), elemental analysis calculated: 72.51% C; 12.78% H; 2.11% N; found: 72.47% C; 12.56% H; 2.03% N].

EXAMPLE 10

1,3-Di-O-(n-hexadecyl)-2-O-(3-isopropylaminopropyl)-glycerol Hydrochloride 1,3-Di-O-(n-hexadecyl)-2-O-(3-aminopropyl)-glycerol hydrochloride (700 mg., 1.1 mmoles) was dissolved in a solution of acetic acid (1.05 ml.), sodium acetate (350 mg., 4.3 mmoles) and acetone (1.3 ml.). Sodium borohydride (1.25 g., 33 mmoles) was added in small portions until TLC analysis showed that all the 3-aminopropyl compound had been consumed. The reaction mixture was then treated with aqueous 2 N sodium hydroxide (20 ml.) and water (20 ml.), and extracted with ether (3×40 ml.). The combined ether extract was dried (MgSO$_4$), filtered, treated with hydrogen chloride gas, and then evaporated in vacuo to a solid, which was recrystallized from hot ethyl acetate [210 mg., solid contained about ½ mole H$_2$O per mole named product, 28% yield, m.p. 72°–73° C., n.m.r. (CDCl$_3$) δ 1.42 (d, 6, —NHCH[C$\underline{H}_3$]$_2$), elemental analysis calculated: 71.82% C; 12.79% H; 2.04% N; found: 71.92% C; 12.46% H; 1.94% N].

EXAMPLE 11

1,2-Di-O-(n-hexadecyl)-3-O-(2-isopropylaminomethyl)-glycerol Hydrochloride

A. 1,2-Di-O-(n-hexadecyl)-3-O-allyl-glycerol

Sodium hydride (1.78 g. of 50 wt. % dispersion in mineral oil, 37 mmoles) was added at 60° C. to a solution of 1,2-di-O-(n-hexadecyl)-glycerol (10 g., 18.5 mmoles) in N,N-dimethylformamide (100 ml.), and the resulting solution stirred for 20 minutes at 60° C. Allyl bromide (4.47 g., 37 mmoles) was then added dropwise and the resulting mixture stirred for 3 hours at 90° C., cooled, cautiosly diluted with water (200 ml.) to quench the reaction, and extracted with ether (3×150 ml.). The combined ether extract was washed with saturated aqueous sodium chloride solution, dried (MgSO$_4$), filtered and evaporated in vacuo to an oil, which was purified by silica gel chromatography (elution with benzene) [10 g., 93% yield, oil, n.m.r. (CDCl$_3$) δ 5.66–6.16 (m, 1, —OCH$_2$C$\underline{H}$=CH$_2$), 5.25 (d of doublets, 2, —OCH$_2$CH=C$\underline{H}_2$) and 4.03 (d, 2, —OC$\underline{H}_2$CH=CH$_2$)].

B. 1,2-Di-O-(n-hexadecyl)-3-O-formylmethyl-glycerol

Osmium tetroxide (90 mg., 0.354 mmoles) was added to a solution of 1,2-di-O-(n-hexadecyl)-3-O-allyl-glycerol (4.5 g., 7.75 mmoles) in tetrahydrofuran:water (3:1, 120 ml.), and the resulting solution stirred for 5 minutes at room temperature. Sodium periodate (9 g., 42 mmoles) was then added and the reaction solution stirred for 16 hours at room temperature under nitrogen. The reaction solution was then diluted with water (150 ml.) and extracted with ether (2×150 ml.). The combined ether extract was washed with water (150 ml.), dried (MgSO$_4$) and evaporated in vacuo to an oil, which was purified by silica gel chromatography (elution with benzene:ethyl acetate) [2.6 g., 57% yield, waxy solid, ir (CHCl$_3$) 1735 cm$^{-1}$, n.m.r. (CDCl$_3$) δ 9.38 (t, J=1 Hz, 1, —OCH$_2$CHO) and 4.07 (d, J=1 Hz, 2, —OCH$_2$CHO)].

C. Title Compound

Sodium cyanoborohydride (0.1 g., 1.6 mmoles) was added to a solution of 1,2-di-O-(n-hexadecyl)-3-O-formylmethyl-glycerol (1.5 g., 2.6 mmoles) and isopropylamine (0.89 g., 15 mmoles) in methanol:tetrahydrofuran (1:1, 50 ml.), and the mixture stirred for two hours at room temperature. The pH was then adjusted to 6 with 5 N methanolic hydrochloric acid, additional sodium cyanoborohydride (0.1 g., 1.6 mmoles) added, and the reaction mixture then stirred for another 60 hours at room temperature, filtered, treated with aqueous 3 N sodium hydroxide (10 ml.) and saturated aqueous sodium chloride solution (200 ml.), and extracted with ether (2×150 ml.). The combined ether extract was dried (MgSO$_4$), filtered and evaporated in vacuo to an oily solid, which was purified by silica gel chromatography (elution with benzene:ethanol) and dissolved in methanol. The solution was treated with hydrogen chloride gas and evaporated in vacuo to yield a solid, which was recrystallized from ethyl acetate [400 mg., solid contained about ¼ mole H$_2$O per mole named product, 23% yield, m.p. 71°–72° C., n.m.r. (CDCl$_3$) δ 1.42 (d, J=6 Hz, 6, —NHCH[CH$_3$]$_2$), elemental analysis calculated: 72.02% C; 12.76% H; 2.10% N; found: 71.89% C; 12.34% H; 2.09% N].

EXAMPLE 12

1,2-Di-O-(n-hexadecyl)-3-O-[2-(2-hydroxyethylamino)-ethyl]-glycerol Hydrochloride In like manner to that described in Example 11 the named compound was prepared by reacting 2-hydroxyethylamine with 1,2-di-O-(n-hexadecyl)-3-O-formylmethyl-glycerol [solid contained about ½ mole H$_2$O per mole named product, m.p. 125°–126° C., elemental analysis calculated: 69.54% C; 12.42% H; 2.07% N; found: 69.62% C; 12.08% H; 2.29% N].

EXAMPLE 13

1,3-Di-O-(n-hexadecyl)-2-O-(4-aminobutyl)-glycerol Hydrochloride

A.
1,3-Di-O-(n-hexadecyl)-2-O-(3-hydroxypropyl)-glycerol

Borane methyl sulfide (BMS) complex (6.5 ml., 68.5 mmoles) was added at 0° to 5° C. to a solution of 1,3-di-O-(n-hexadecyl)-2-O-allyl-glycerol (10.82 g., 18.6 mmoles, prepared as in Example 11A) in hexane (190 ml.), and the resulting solution stirred for 3 hours at room temperature. The reaction solution was then cooled again to 0° to 5° C. and ethanol (17.3 ml.) added dropwise to decompose residual BMS. The reaction solution was then treated with aqueous 3 N sodium hydroxide (13 ml.) and 30 wt. % aqueous hydrogen peroxide (11 ml.), stirred for 16 hours at reflux, cooled, and poured into ice water containing sodium bisulfite. The ice water solution was stirred until it gave a negative starch-iodide test for peroxides, and then extracted with ether (3×200 ml.). The combined ether extract was washed with water (200 ml.), washed with saturated aqueous sodium chloride solution (200 ml.), dried (MgSO$_4$), filtered and evaporated in vacuo. The resulting product was purified by silica gel chromatography (elution with benzene:ethanol) [5 g., 45% yield, m.p. 29° C., n.m.r. (CDCl$_3$) δ 3.80 (t, J=5 Hz, 2, —OCH$_2$CH$_2$CH$_2$OH) and 3.75 (t, J=5 Hz, 2, —OCH$_2$CH$_2$CH$_2$OH)].

B.
1,3-Di-O-(n-hexadecyl)-2-O-[3-(p-tosyloxy)propyl]-glycerol 1,3-Di-O-(n-hexadecyl)-2-O-(3-hydryoxypropyl)-glycerol (8.0 g., 13.4 mmoles) was added at 10° C. to a solution of p-toluenesulfonyl chloride (5.25 g., 27.5 mmoles) and pyridine (10 ml. in methylene chloride (200 ml.), and the mixture stirred for 60 hours at room temperature. Water (200 ml.) was then added, the methylene chloride and aqueous phases separated, and the latter extracted with methylene chloride (2×150 ml.). The three methylene chloride layers were combined, washed with water (2×150 ml.), dried (MgSO$_4$), filtered and evaporated in vacuo. The resulting tosylate was purified by silica gel chromatography (elution with benzene) [3.0 g., 30% yield, oil, ir (CHCl$_3$) 1130 and 1350 cm$^{-1}$, n.m.r. (CDCl$_3$) δ 7.53 (q, 4, protons on phenyl ring), 4.15 (t, 2, —SO$_3$CH$_2$CH$_2$CH$_2$O—), 3.63 (t, 2, —SO$_3$CH$_2$CH$_2$CH$_2$O—), 3.42 (m, 9, —OCH[CH$_2$OCH$_2$C$_{15}$H$_{31}$]$_2$), 2.45 L (s, 3, Ar—CH$_3$), 1.90 (m, 2, —SO$_3$CH$_2$CH$_2$CH$_2$O—) and 0.90–1.50 (m, 62, aliphatic protons)].

C.
1,3-Di-O-(n-hexadecyl)-2-O-(3-cyanopropyl)-glycerol 1,3-Di-O-(n-hexadecyl)-2-O-[3-(p-tosyloxy)propyl]-glycerol (3.0 g., 4.0 mmoles) was dissolved in a solution of sodium cyanide (0.5 g., 10 mmoles) in N,N-dimethylformamide (50 ml.), and the resulting solution stirred for 16 hours at 80° C., cooled, diluted with water (100 ml.) and extracted with ether (3×100 ml.). The combined ether extract was washed consecutively with 1 N hydrochloric acid (3×75 ml.), saturated aqueous sodium bicarbonate solution (3×75 ml.), water (75 ml.) and saturated aqueous sodium chloride solution (75 ml.), then dried (MgSO$_4$), filtered and evaporated in vacuo to yield a waxy solid that was used in the next step without further purification [2.0 g., 83% yield, ir (CHCl$_3$) 2250 cm$^{-1}$].

D. Title Compound

Lithium aluminum hydride (800 mg., 21 mmoles) was added to a solution of 1,3-di-O-(n-hexadecyl)-2-O-(3-cyanopropyl)-glycerol (2.0 g., 3.3 mmoles) in ether (100 ml.), and the mixture stirred for 60 hours at room temperature. Enough water to quench the reaction was added cautiously, followed by an additional 100 ml. of water. The resulting mixture was stirred for another hour at room temperature and then extracted with ether (3×100 ml.). The combined ether extract was washed with saturated aqueous sodium chloride solution (3×75 ml.), dried (MgSO$_4$), filtered and evaporated in vacuo to an oil, which was purified by silica gel chromatography (elution with benzene:ethanol) and then dissolved in ethanol. The solution was treated with hydrogen chloride gas and then evaporated in vacuo to yield a solid, which was recrystallized from ethyl acetate [444 mg., 21% yield, m.p. 61.5°–63.5° C., n.m.r. (CDCl$_3$) δ 3.67 (t, 2, —OC$\underline{H}_2$CH$_2$CH$_2$CH$_2$NH$_2$), 3.55 (m, 9, —OC$\underline{H}$[C$\underline{H}_2$OCH$_2$C$_{15}$H$_{31}$]$_2$), 3.10 (t, 2, —OCH$_2$CH$_2$CH$_2$C$\underline{H}_2$NH$_2$), 1.50–2.00 (m, 4, —OCH$_2$C$\underline{H}_2$C$\underline{H}_2$CH$_2$NH$_2$) and 0.80–1.50 (m, 62, aliphatic protons), elemental analysis calculated: 72.23% C; 12.74% H; 2.16% N; found: 72.53% C; 12.42% H; 2.10% N].

EXAMPLE 14

1,2-Di-O-(n-hexadecyl)-3-O-(3-aminomethylbenzyl)-glycerol Hydrochloride

A.

1,2-Di-O-(n-hexadecyl)-3-O-(3-cyanobenzyl)-glycerol with ether (3×50 ml.). The combined ether extract was dried (MgSO$_4$), filtered and evaporated in vacuo to an oil, which was purified by silica gel chromatography (elution with benzene:ethanol) and then dissolved in ethyl acetate. The solution was treated with hydrogen chloride gas and then evaporated in vacuo to yield a solid, which was recrystallized from ethyl acetate [220 mg., 21% yield, m.p. 88°–90° C., elemental analysis calculated: 74.14% C; 11.87% H; 2.01% N; found: 74.35% C; 11.54% H; 2.15% N].

EXAMPLES 15–26

In like manner to that described in Example 14 the following compounds were prepared by using the appropriate 1,3- or 1,2-di-O-(n-higher alkyl or alkenyl)-glycerol and cyanobenzyl bromide as starting materials:

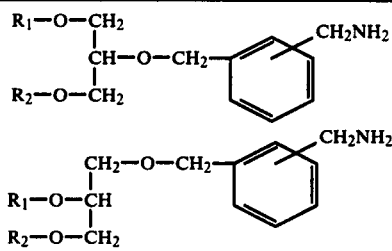

| Ex. No. | Structure | R$_1$ | R$_2$ | Substitution on Phenyl Ring | Molecular Formula | M.P. (°C.) | Calculated (%) C | H | N | Found (%) C | H | N |
| --- | --- | --- | --- | --- | --- | --- | --- | --- | --- | --- | --- | --- |
| 15 | I | n-hexadecyl | n-hexadecyl | ortho | C$_{43}$H$_{81}$O$_3$N . HCl | 71–73 | 74.14 | 11.87 | 2.01 | 73.89 | 11.43 | 1.99 |
| 16 | I | n-hexadecyl | n-hexadecyl | meta | C$_{43}$H$_{81}$O$_3$N . HCl | 77–79 | 73.20 | 11.85 | 1.98 | 73.17 | 11.53 | 2.28 |
| 17 | I | n-hexadecyl | n-hexadecyl | para | C$_{43}$H$_{81}$O$_3$N . HCl . H$_2$O | 77–78 | 72.28 | 11.83 | 1.96 | 72.52 | 11.46 | 1.90 |
| 18 | II | n-tetradecyl | n-tetradecyl | ortho | C$_{39}$H$_{73}$O$_3$N . HCl . ¼ H$_2$O | 71–72 | 72.63 | 11.48 | 2.17 | 72.62 | 11.81 | 2.43 |
| 19 | II | n-hexadecyl | n-hexadecyl | ortho | C$_{43}$H$_{81}$O$_3$N . HCl | 79–80 | 74.14 | 11.87 | 2.01 | 73.94 | 11.25 | 2.02 |
| 20 | II | n-tetradecyl | n-tetradecyl | meta | C$_{39}$H$_{73}$O$_3$N . HCl | 87–88 | 73.14 | 11.65 | 2.19 | 72.86 | 11.44 | 2.11 |
| 21 | II | n-octadecyl | n-octadecyl | meta | C$_{47}$H$_{89}$O$_3$N . HCl | 73–75 | 74.99 | 12.06 | 1.86 | 74.97 | 11.73 | 1.83 |
| 22 | II | n-octadec-9-enyl | n-octadec-9-enyl | meta | C$_{47}$H$_{85}$O$_3$N . HCl . ½ H$_2$O | oil | 74.50 | 11.57 | 1.85 | 74.40 | 11.08 | 2.08 |
| 23 | II | n-tetradecyl | n-tetradecyl | para | C$_{39}$H$_{73}$O$_3$N . HCl | 132–135 | 73.14 | 11.65 | 2.19 | 72.84 | 11.30 | 2.26 |
| 24 | II | n-hexadecyl | n-hexadecyl | para | C$_{43}$H$_{81}$O$_3$N . HCl | 117–119 | 74.14 | 11.87 | 2.01 | 74.33 | 11.55 | 2.15 |
| 25 | II | n-octadecyl | n-octadecyl | para | C$_{47}$H$_{89}$O$_3$N . HCl | 67–69 | 74.99 | 12.06 | 1.86 | 74.50 | 11.30 | 1.91 |
| 26 | II | n-octadec-9-enyl | n-octadec-9-enyl | para | C$_{47}$H$_{85}$O$_3$N . HCl . ¾ H$_2$O | oil | 74.06 | 11.54 | 1.83 | 74.00 | 10.99 | 1.93 |

Sodium hydride (1.056 g. of 50 wt. % mineral oil dispersion, 22 mmoles) was added to a solution of 1,2-di-O-(n-hexadecyl)-glycerol (9.73 g., 18 mmoles) in tetrahydrofuran (150 ml.) and the resulting solution stirred for 20 minutes at room temperature under nitrogen. m-Cyanobenzyl bromide (4.0 g., 20 mmoles) was added and the reaction mixture stirred overnight at room temperature under nitrogen. Water (200 ml.) was then added cautiously and the resulting mixture extracted with ethyl acetate (3×150 ml.). The combined ethyl acetate extract was dried (MgSO$_4$), filtered and evaporated in vacuo to an oil (12 g.), which was purified by silica gel chromatography (elution with benzene:hexane) [8.0 g., 68% yield, oil, ir (CHCl$_3$) 2230 cm$^{-1}$].

B. Title Compound

A solution of 1,2-di-O-(n-hexadecyl)-3-O-(3-cyanobenzyl)-glycerol (1.0 g., 1.5 mmoles) in ether (10 ml.) was slowly added under nitrogen to a suspension of lithium aluminum hydride (0.057 g., 1.5 mmoles) in ether (40 ml.), and the resulting mixtures stirred for one hour at reflux under nitrogen and then cooled. Water (50 ml.) was added cautiously and the mixture extracted

EXAMPLE 27

1,2-Di-O-(n-hexadecyl)-3-O-(4-aminomethylphenyl)-glycerol Hydrochloride

A. 1,2-Di-O-(n-hexadecyl)-3-O-(p-tosyl)-glycerol

In like manner to that described in Example 13B the named compound was prepared by reacting 1,2-di-O-(n-hexadecyl)-glycerol with p-toluenesulfonyl chloride. Purification was accomplished by recrystallization from ethyl acetate [m.p. 53°–55° C., ir (CHCl$_3$) 1360 and 1180 cm$^{-1}$].

B.

1,2-Di-O-(n-hexadecyl)-3-O-(4-cyanophenyl)-glycerol

A mixture of 1,2-di-O-(n-hexadecyl)-3-O-(p-tosyl)-glycerol (1.4 g., 2.0 mmoles), sodium 4-cyanophenolate (0.5 g., 3.5 mmoles) and xylene (100 ml.) was stirred for 16 hours at reflux. Since the reaction was not yet complete the xylene was removed by distillation and replaced by N,N-dimethylformamide (100 ml.), and the resulting solution stirred for another 16 hours at 150° C.

The reaction solution was then cooled, diluted with water (100 ml. and extracted with ether (2×100 ml.). The combined ether extract was washed consecutively with 3 N hydrochloric acid (100 ml.), 10 wt. % aqueous sodium bicarbonate solution (100 ml.) and water (100 ml.), dried (MgSO₄), filtered and evaporated in vacuo to an oil, which was purified by silica gel chromatography (elution with benzene) [0.65 g., 50% yield, m.p. 53°–55° C., ir (CHCl₃) 2210 cm$^{-1}$].

C. Title Compound 1,2-Di-O-(n-hexadecyl)-3-O-(4-cyanophenol)-glycerol (0.60 g., 0.93 mmole) was added to a suspension of lithium aluminum hydride (0.3 g., 7.9 mmoles) in ether (25 ml.), and the resulting mixture stirred for 30 minutes at room temperature. Water (25 ml.) was then added cautiously, the ether and aqueous phases separated, and the latter extracted with ether (3×25 ml.) and ethyl acetate (25 ml.). The five organic extracts were combined, dried (MgSO₄), filtered and evaporated in vacuo to an oil, which was dissolved in ether. The solution was treated with hydrogen chloride gas, causing precipitation of a solid [0.41 g., 64% yield, m.p. 110°–112° C., n.m.r. (CDCl₃) δ 4.02 (s, 2, —C$\underline{H}_2$NH₂), elemental analysis calculated: 73.91% C; 11.81% H; 2.05% N; found: 73.62% C; 11.71% H; 2.14% N].

EXAMPLES 28–30

In like manner to that described in Example 27 B-C the following compounds were prepared from the appropriate tosylate (prepared as in Example 27A) and sodium cyanophenolate:

formamide (20 ml.). The resulting mixture was stirred for one hour at 90° C. and then poured into ice water (150 ml.), causing the formation of solids which were isolated by filtration, purified by silica gel chromatography (elution with benzene:ethanol) and then dissolved in ethyl acetate. The solution was treated with hydrogen chloride gas and then evaporated in vacuo to yield a solid, which was recrystallized from ethyl acetate [0.29 g., 8% yield, m.p. 78°–80° C., n.m.r. (CDCl₃) δ 4.24 (s, 2, Ar—C$\underline{H}_2$NH—) and 4.37 (s, 2, Ar—C$\underline{H}_2$NH₂), elemental analysis calculated: 70.55% C; 11.57% H; 3.83% N; found: 70.64% C; 11.29% H; 3.62% N].

EXAMPLE 33

1,2-Di-O-(n-hexadecyl)-3-O-(3-isopropylamino-2-hydroxypropyl)-glycerol Hydrochloride

A.

1,2-Di-O-(n-hexadecyl)-3-O-(2,3-epoxypropyl)-glycerol

A solution of 1,2-di-O-(n-hexadecyl)-3-allyl-glycerol (5.8 g., 10.0 mmoles) and m-chloroperbenzoic acid (1.86 g., 10.8 mmoles) in benzene (50 ml.) was stirred at reflux for 16 hours. The reaction mixture was then cooled, treated with saturated aqueous sodium bisulfite solution (10 ml.) and saturated aqueous sodium bicarbonate solution (50 ml.), and extracted with ether (3×50 ml.). The combined ether extract was washed with water (100 ml.), washed with saturated aqueous sodium chloride solution (100 ml.), dried (MgSO₄), filtered and evaporated in vacuo to an oil (4.9 g., 82% yield, olefinic pro-

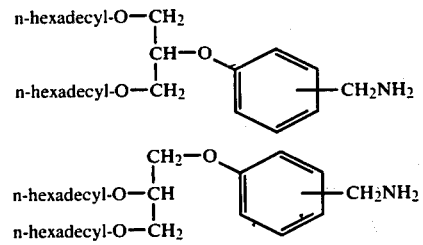

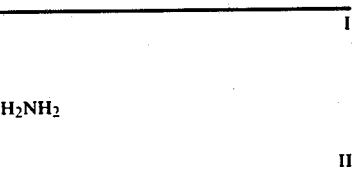

| Example Number | Structure | Substitution on Phenyl Ring | Molecular Formula | M.P.(°C.) | Calculated (%) | | | Found (%) | | |
|---|---|---|---|---|---|---|---|---|---|---|
| | | | | | C | H | N | C | H | N |
| 28 | I | meta | C₄₂H₇₉O₃N . HCl | 78–80 | 73.91 | 11.81 | 2.05 | 74.11 | 11.64 | 2.44 |
| 29 | I | para | C₄₂H₇₉O₃N . HCl | 120–122 | 73.91 | 11.81 | 2.05 | 73.94 | 11.37 | 2.04 |
| 30 | II | meta | C₄₂H₇₉O₃N . HCl | 84–86 | 73.91 | 11.81 | 2.05 | 74.00 | 11.34 | 2.04 |

EXAMPLE 31

1,2-Di-O-(n-hexadecyl)-3-O-[4-(3-aminopropyl)-phenyl]-glycerol Hydrochloride

In like manner to that described in Example 27 the named compound was prepared by using sodium 4-(2-cyanoethyl)phenolate in place of sodium 4-phenolate (m.p. 153°–155° C., elemental analysis calculated: 74.37% C; 11.91% H; 1.97% N; found: 74.13% C; 11.44% H; 2.08% N).

EXAMPLE 32

1,2-Di(n-hexadecyloxy)-3-(3-aminomethylbenzylamino)-propane Dihydrochloride 1,2-Di-O-(n-hexadecyl)-3-O-(p-tosyl)-glycerol (3.48 g., 5.0 mmoles) was added to a solution of m-xylylenediamine (0.68 g., 5.0 mmoles) in N,N-dimethyltons absent by n.m.r. analysis), which was purified by silica gel chromatography (elution with benzene:ethyl acetate) (4.2 g., 70% yield, oil-solidified on standing).

B. Title Compound

A solution of 1,2-di-O-(n-hexadecyl)-3-O-(2,3-epoxypropyl)-glycerol (2.0 g., 3.35 mmoles) in isopropylamine (40 ml.) was heated in a stainless steel bomb for 16 hours at 100° C., cooled, concentrated in vacuo and dissolved in ether (100 ml.). The ether solution was washed with 1 N hydrochloric acid (100 ml.), dried (MgSO₄), filtered, treated with charcoal, filtered again, and then cooled by immersion of the flask in a Dry Ice-acetone bath, causing formation of a precipitate. The precipitate was isolated by filtration (1.3 g.) and purified by silica gel chromatography (elution with benzene:ethanol) [720 mg., solid contained about ½ mole H₂O per mole named product, 31% yield, m.p. 55°-57° C., n.m.r. (CDCl₃) δ 1.45 (d, 6, —NHCH[C$\underline{H}$₃]₂), elemental analysis calculated: 70.19% C; 12.50% H; 2.00% N; found: 70.10% C; 12.19% H; 1.87% N].

EXAMPLES 34-37

In like manner to that described in Example 33B the following compounds were prepared by reacting the appropriate 2,3-epoxide (prepared as in Example 33A) and alkylamine:

C$\underline{H}$OCHCH₂NH₂), 3.33-3.73 (m, 11, C₁₅H₃₁C$\underline{H}$₂OC$\underline{H}$₂C$\underline{H}$[OC$\underline{H}$₂C₁₅H₃₁]C$\underline{H}$₂OC$\underline{H}$₂—), 3.03-3.25 (m, 2, —OCH₂CHOHC$\underline{H}$₂NH₂) and 0.87-1.67 (m, 62, aliphatic protons), elemental analysis calculated: 66.48% C; 12.33% H; 2.04% N; found: 66.68% C; 11.85% H; 2.02% N].

EXAMPLE 39

1,3-Di-O-(n-hexadecyl)-2-O-(3-amino-2-hydroxypropyl)-glycerol

In like manner to that described in Example 38 the

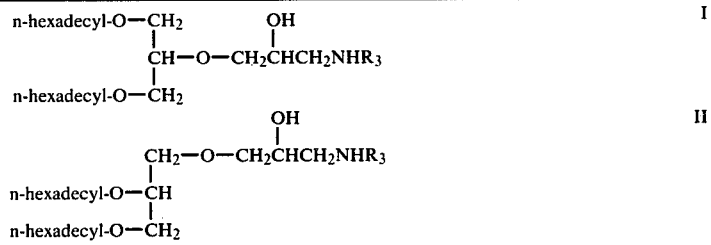

| Example Number | Structure | R₃ | Molecular Formula | M.P. (°C.) | Calculated (%) C | H | N | Found (%) C | H | N |
|---|---|---|---|---|---|---|---|---|---|---|
| 34 | I | —CH₂CH₃ | C₄₀H₈₃O₄N . HCl | 53–54 | 68.97 | 12.44 | 2.01 | 69.35 | 12.08 | 1.94 |
| 35 | I | —CH(CH₃)₂ | C₄₁H₈₅O₄N . HCl | 67–68 | 71.10 | 12.52 | 2.02 | 70.54 | 12.18 | 2.05 |
| 36 | I | —C(CH₃)₃ | C₄₂H₈₇O₄N . HCl | 60–61 | 71.39 | 12.55 | 1.98 | 71.55 | 12.35 | 1.79 |
| 37 | II | —C(CH₃)₃ | C₄₂H₈₇O₄N . HCl . ½ H₂O | 50–51 | 70.49 | 12.53 | 1.96 | 70.66 | 12.31 | 1.83 |

EXAMPLE 38

1,2-Di-O-(n-hexadecyl)-3-O-(3-amino-2-hydroxypropyl)-glycerol Hydrochloride

A.

1,2-Di-O-(n-hexadecyl)-3-O-(3-azido-2-hydroxypropyl)-glycerol

A solution of sodium azide (0.5 g., 7.7 mmoles) in water (5 ml.) was added to a refluxing solution of 1,2-di-O-(n-hexadecyl)-3-O-(2,3-epoxypropyl)-glycerol (3.3 g., 5.5 mmoles) in 1,4-dioxane (100 ml.), and the resulting solution stirred at reflux for 16 hours. Since the reaction was not yet complete, additional sodium azide (0.5 g., 7.7 mmoles) was added and the reaction stirred at reflux for another 16 hours. The reaction solution was then cooled, concentrated in vacuo, diluted with water (100 ml.) and extracted with ether (3×100 ml.). The combined ether extract was washed with water (100 ml.), dried (MgSO₄), filtered and evaporated in vacuo to an oil which solidified on standing [2.2 g., 62% yield, ir (CHCl₃) 2105 cm⁻¹].

B. Title Compound

Lithium aluminum hydride (300 mg., 7.9 mmoles) was added to a solution of 1,2-di-O-(n-hexadecyl)-3-O-(3-azido-2-hydroxypropyl)-glycerol (2.2 g., 3.4 mmoles) in ether (100 ml.), and the resulting mixture stirred for one hour at room temperature. Ethanol (5 ml.) and water (200 ml.) were added to quench the reaction, and the mixture then extracted with ether (2×100 ml.). The combined ether extract was dried (MgSO₄), filtered and evaporated in vacuo. The resulting product was purified by silica gel chromatography (elution with benzene:ethanol) and then converted to the hydrochloride salt [800 mg., solid contained about 2 moles H₂O per mole named product, 34% yield, m.p. 149°-150° C., n.m.r. (CDCl₃) δ 4.00-4.35 (m, 1, —OCH₂- named compound was prepared from 1,3-di-O-(n-hexadecyl)-2-O-(2,3-epoxypropyl)-glycerol (prepared as in Example 33A) (free base, m.p. 61°-63° C., elemental analysis calculated: 74.33% C; 12.96% H; 2.28% N; found: 74.49% C; 13.10% H; 2.12% N).

EXAMPLE 40

1,2-Di-O-(n-hexadecyl)-3-O-(2-aminopropyl)-glycerol Hydrochloride

A.

1,2-Di-O-(n-hexadecyl)-3-O-[2-(p-tosyloxy)propyl]-glycerol

In like manner to that described in Example 13A and B, 1,2-di-O-(n-hexadecyl)-3-O-allyl-glycerol was reacted with BMS, and the resulting 2-hydroxypropyl and 3-hydroxypropyl compounds converted to their corresponding tosylates. A separation was not attempted at this stage; the mixture of tosylates was used directly in the next step.

B.

1,2-Di-O-(n-hexadecyl)-3-O-(2-azidopropyl)-glycerol

The resulting mixture of tosylates (3.0 g., 4.0 mmoles) was dissolved in N,N-dimethylacetamide (50 ml.) and treated with a solution of sodium azide (0.326 g., 5.0 mmoles) in water (5 ml.) for 16 hours at 90° C. The reaction solution was then cooled, diluted with water (200 ml.), and extracted with ether (2×150 ml.). The combined ether extract was washed with water, dried (MgSO₄), filtered, and evaporated in vacuo to an oil [2 g., 81% yield, ir (CHCl₃) 2100 cm⁻¹], a mixture of the 2-azidopropyl and 3-azidopropyl compounds, which was used without further purification in the next step.

C. Title Compound

The resulting mixture of azides (2 g., 3.2 mmoles) was dissolved in ether (100 ml.), treated with lithium aluminum hydride (0.4 g., 10.5 mmoles), and allowed to stir for 2 hours at room temperature. Excess hydride was destroyed by cautious addition of ethanol (10 ml.) and water (150 ml.), and the mixture then extracted with ether (2×100 ml.). The combined ether extract was dried (MgSO$_4$), filtered, and concentrated in vacuo to an oil (1.8 g.), which was purified by silica gel chromatography (elution with benzene:ethanol) and then converted to the hydrochloride salt by dissolution and treatment with hydrogen chloride gas. The salt was recrystallized from ethyl acetate (0.21 g., solid contained about ½ mole H$_2$O per mole named product, 10% yield, m.p. 56°–58° C. elemental analysis calculated: 71.03% C; 12.70% H; 28.1% N; found: 71.11% C; 12.91% H; 2.16% N).

EXAMPLE 41

1,2-Di-O-(n-octadecyl)-3-O-(2-aminopropyl)-glycerol Hydrochloride

In like manner to that described in Example 40A, 1,2-di-O-(n-octadecyl)-3-O-(2-hydroxypropyl)-glycerol was prepared from 1,2-di-O-(n-octadecyl)-3-O-allyl-glycerol. The named compound was prepared from 1,2-di-O-(n-octadecyl)-3-O-(2-hydroxypropyl)glycerol in like manner to that described in Example 40 B-C (solid contained about 1 mole H$_2$O per mole named product, m.p. 65°–67° C., elemental analysis calculated: 71.19% C; 12.80% H; 1.98% N; found: 71.12% C; 12.52% H; 1.92% N).

EXAMPLE 42

1,2-Di(n-hexadecyloxy)-3-aminopropane Hydrochloride

In like manner to that described in Example 40B, 1,2-di-O-(n-hexadecyl)-3-O-(p-tosyl)-glycerol was converted to 1,2-di(n-hexadecyloxy)-3-azidopropane. This intermediate was converted to the title compound in like manner to that described in Example 40C (m.p. 78°–80° C., elemental analysis calculated: 72.93% C; 12.94% H; 2.43% N; found: 73.08% C; 13.08% H; 2.65% N).

EXAMPLE 43

1,3-Di(n-hexadecyloxy)-2-aminopropane Hydrochloride

In like manner to that described in Example 42 the named compound was prepared from 1,3-di-O-(n-hexadecyl)-2-O-(p-tosyl)-glycerol (prepared as in Example 27A) (m.p. 58°–60° C., elemental analysis calculated: 72.93% C; 12.94% H; 2.43% N; found: 72.65% C; 13.02% H; 2.59% N).

EXAMPLE 44

1,2-Di(n-hexadecyloxy)-4-aminobutane Hydrochloride

In like manner to that described in Example 42 the named compound was prepared by using sodium cyanide in place of sodium azide (m.p. 86°–87° C., elemental analysis calculated: 73.25% C; 12.97% H; 2.37% N; found: 73.52% C; 12.64% H; 2.50% N).

EXAMPLE 45

1,3-Di(n-hexadecyloxy)-2-(3-aminopropylamino)propane Dihydrochloride

A.

1,3-Di(n-hexadecyloxy)-2-(2-cyanoethylamino)propane

A mixture of 1,3-di(n-hexadecyloxy)-2-aminopropane (500 mg., 0.93 mmoles), acrylonitrile (75 ml.) and 2 wt. % aqueous sodium hydroxide solution (75 ml.) was heated to 60° C. Tetrabutyl ammonium hydroxide (1 ml. of 40 wt. % aqueous solution) was then added and the resulting mixture stirred for 15 minutes at 90° C. The reaction mixture was then cooled, causing precipitation of solids, which were isolated by filtration and found (TLC) to contain a large quantity of unreacted starting material. Using fresh acrylonitrile and aqueous sodium hydroxide solution in each cycle, the solids were treated two more times by the above procedure. The third cycle solid product was purified by silica gel chromatography (elution with toluene:ethyl acetate) [200 mg., 36% yield, m.p. 45°–46° C., ir (CHCl$_3$) 2250 cm$^{-1}$, n.m.r. (CDCl$_3$) δ 3.07 (t, 2, —NHC$\underline{H}_2$CH$_2$CN) and 2.53 (t, 2, —NHCH$_2$C$\underline{H}_2$CN)].

B. Title Compound

A mixture of 1,3-di(n-hexadecyloxy)-2-(2-cyanoethylamino)-propane (200 mg., 0.34 mmoles), tetrahydrofuran (10 ml.), ethanol (20 ml.) and Raney nickel catalyst (0.2 g.) was saturated with ammonia gas and then hydrogenated (50 psi) for about 4 hours at room temperature. The reaction mixture was then filtered and evaporated in vacuo to an oil, which was purified by silica gel chromatography (elution with toluene:ethyl acetate: ethanol: methanol) and then dissolved in ethyl acetate. The solution was treated with hydrogen chloride gas, causing precipitation of solids [10 mg., solid contained about 2.5 moles H$_2$O per mole named product, 4% yield, m.p. 235°–236° C., elemental analysis calculated: 63.65% C; 12.51% H; 3.90% N; found: 63.60% C; 11.84% H; 3.75% N].

EXAMPLE 46

1,2-Di-O-(n-hexadecyl)-3-O-(4-amidinophenyl)-glycerol Hydrochloride

A solution of 1,2-di-O-(n-hexadecyl)-3-O-(4-cyanophenyl)-glycerol (3.5 g., 5.45 mmoles), ethanol (10 ml.) and 1,4-dioxane (100 ml.) was saturated with hydrogen chloride gas at 0° C., and allowed to react for 16 hours at ambient temperature. The reaction solution was then evaporated in vacuo to an oil, the oil dissolved in ethanol (100 ml.), and the resulting solution saturated with ammonia gas, stirred for 3 hours at reflux, diluted with water (150 ml.), evaporated in vacuo to remove the majority of the ethanol, and extracted with chloroform (3×150 ml.). The combined chloroform extract was dried (MgSO$_4$), filtered and evaporated in vacuo to yield a solid, which was purified by silica gel chromatography (elution with benzene:ethanol) and then dissolved in ethyl acetate. The solution was treated with hydrogen chloride gas and then evaporated in vacuo to yield a solid, which was recrystallized from ethyl acetate [1.0 g., 26% yield, m.p. 220°–222° C., ir (CHCl$_3$) 1670 cm$^{-1}$, elemental analysis calculated: 72.53% C; 11.45% H; 4.03% N; found: 72.67% C; 11.38% H; 4.12% N].

EXAMPLE 47

1,2-Di-O-(n-hexadecyl)-3-O-(3-amidinobenzyl)-glycerol Hydrochloride

The named compound was prepared from 1,2-di-O-(n-hexadecyl)-3-O-(3-cyanobenzyl)-glycerol in like manner to that described in Example 46 [solid contained about 2 moles $H_2O$ per mole named product, 20% yield, m.p. 155°–157° C., ir ($CHCl_3$) 1670 $cm^{-1}$, elemental analysis calculated: 69.27% C; 11.48% H; 3.76% N; found: 69.11% C; 10.63% H; 3.83% N].

EXAMPLE 48

1,2-Di-O-(n-hexadecyl)-3-O-[3-(1-hydroxy-2-t-butylaminoethyl)-benzyl]-glycerol Hydrochloride

A. 1,2-Di-O-(n-hexadecyl)-3-O-(3-formylbenzyl)-glycerol

A solution of 1,2-di-O-(n-hexadecyl)-3-O-(3-cyanobenzyl)-glycerol (5.0 g., 7.6 mmoles) and diisobutylaluminum hydride (1.17 g., 8.2 mmoles) in benzene (25 ml.) was stirred for 16 hours at ambient temperature. The reaction mixture was treated with methanol (4.22 ml.) and water (2.5 ml.) and stirred to decompose unreacted hydride, and then filtered and extracted with benzene (3×25 ml.). The combined benzene extract was dried ($Na_2SO_4$), filtered and evaporated in vacuo to an oil, which was purified by silica gel chromatography (elution with benzene) [2.0 g., 40% yield, oil, ir ($CHCl_3$) 1700 $cm^{-1}$, n.m.r. ($CDCl_3$) δ 10.1 (s, 1, —ArC$\underline{H}$O)].

B. 1,2-Di-O-(n-hexadecyl)-3-O-[3-(1,2-epoxyethyl)benzyl]-glycerol

A suspension of sodium hydride (3.23 g. of a 57 wt. % dispersion in mineral oil, 67 mmoles) in dimethylsulfoxide (117 ml.) was heated under a nitrogen atmosphere at 70° to 75° C. until hydrogen evolution stopped (45 min.). Tetrahydrofuran (88 ml.) was added and the mixture cooled to 0° to 5° C. Trimethylsulfonium iodide (13.67 g., 67 mmoles) was then added in portions, followed by rapid addition of a solution of 1,2-di-O-(n-hexadecyl)-3-O-(3-formylbenzyl)-glycerol (7.0 g., 10.6 mmoles) in tetrahydrofuran (58 ml.). The resulting mixture was stirred for 16 hours at room temperature, poured into water (200 ml.) and extracted with ether (3×180 ml.). The combined ether extract was washed with water (2×100 ml.) and saturated aqueous sodium chloride solution (100 ml.), dried ($MgSO_4$), filtered and evaporated in vacuo to an oil (7.0 g., 98% yield), which was sufficiently pure to be used in the next step.

C. Title Compound

A mixture of t-butylamine (30 ml.) and 1,2-di-O-(n-hexadecyl)-3-O-[3-(1,2-epoxyethyl)-benzyl]-glycerol (2.0 g., 3.0 mmoles) was heated for 9 hours at 100° C. in a steel bomb. The reaction mixture was cooled, t-butylamine removed by evaporation in vacuo, and the resulting oil purified by silica gel chromatography (elution with benzene:ethanol) and then dissolved. The solution was saturated with hydrogen chloride gas and then evaporated in vacuo to yield a solid, which was recrystallized from ethyl acetate [630 mg., solid contained about 1 mole $H_2O$ per mole named product, 27% yield, m.p. 49°–51° C., n.m.r. ($CDCl_3$) δ 1.47 (s, 9, —C[C$\underline{H}_3$]$_3$), elemental analysis calculated: 71.99% C; 11.83% H; 1.75% N; found: 71.86% C; 11.30% H; 1.69% N].

EXAMPLE 49

1,3-Di-O-(n-hexadecyl)-2-O-[3-(1-hydroxy-2-t-butylaminoethyl)-benzyl]-glycerol Hydrochloride In like manner to that described in Example 48 A-B, 1,3-di-O-(n-hexadecyl)-2-O-(3-cyanobenzyl)-glycerol (prepared as in Example 14A) was converted to 1,3-di-O-(n-hexadecyl)-2-O-[3-(1,2-epoxyethyl)-benzyl]-glycerol. The title compound was prepared by reacting said epoxy compound with t-butylamine in like manner to that described in Example 48C (solid contained about 1 mole $H_2O$ per mole named product, m.p. 43°–45° C., elemental analysis calculated: 71.99% C; 11.83% H; 1.75% N; found: 72.06% C; 11.43% H; 1.71% N).

EXAMPLE 50

1,2-Di-O-(n-hexadecyl)-3-O-[3-(1-hydroxy-2-isopropylaminoethyl)-benzyl]-glycerol Hydrochloride In like manner to that described in Example 48C the named compound was prepared by using isopropylamine in place of t-butylamine (solid contained about ¾ mole $H_2O$ per mole named product, m.p. 53°–55° C., elemental analysis calculated: 72.17% C; 11.79% H; 1.79% N; found: 72.11% C; 11.55% H; 1.92% N).

EXAMPLE 51

1-[2,3-Di(n-hexadecyloxy)propyl]-4-aminomethyl-4-phenylpiperidine Dihydrochloride

A. 1-[2,3-Di(n-hexadecyloxy)propyl]-4-cyano-4-phenylpiperidine

A mixture of 1,2-di-O-(n-hexadecyl)-3-O-(p-tosyl)-glycerol (6.96 g., 10 mmoles), 4-cyano-4-phenylpiperidine hydrochloride (2.23 g., 10 mmoles), triethylamine (2 ml.) and N,N-dimethylformamide (40 ml.) was stirred for 16 hours at 95° to 100° C. The reaction mixture was then cooled, diluted with water (200 ml.) and extracted with ethyl acetate (3×150 ml.). The combined ethyl acetate extract was dried ($MgSO_4$), filtered and evaporated in vacuo to an oil (6 g.), which was purified by column chromatography (elution with benzene:ethyl acetate) [oil, ir ($CHCl_3$) 2220 $cm^{-1}$].

B. Title Compound

A solution of 1-[2,3-di(n-hexadecyloxy)propyl]-4-cyano-4-phenylpiperidine (2.5 g., 3.6 mmoles) in ether (100 ml.) was treated with lithium aluminum hydride (0.4 g., 10.5 mmoles), and the resulting mixture stirred for 4 hours at room temperature. The reaction mixture was treated cautiously with water (100 ml.) and extracted with ether (3×100 ml.). The combined ether extract was dried ($MgSO_4$), filtered and evaporated in vacuo to an oil, which was purified by silica gel chromatography (elution with benzene:ethanol) and then dissolved. The solution was treated with hydrogen chloride gas and then evaporated in vacuo to yield a solid, which was recrystallized from ethyl acetate (1.1 g., solid contained about ¾ mole $H_2O$ per mole named product, 40% yield, m.p. 132°–134° C., elemental analysis calculated: 70.60% C; 11.53% H; 3.50% N; found: 70.74% C; 11.34% H; 3.40% N).

EXAMPLES 52-54

In like manner to that described in Example 51 the following compounds were prepared from the appropriate 1,2-di-O-(n-alkyl or alkenyl)-3-O-(p-tosyl)-glycerol (prepared as in Example 27A):

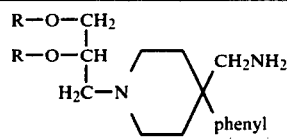

| Example Number | R | Molecular Formula | M.P.(°C.) | Calculated (%) C | H | N | Found (%) C | H | N |
|---|---|---|---|---|---|---|---|---|---|
| 52 | n-tetradecyl | $C_{43}H_{80}O_2N_2 \cdot 2HCl$ | 140-142 | 69.46 | 11.25 | 3.75 | 69.45 | 11.00 | 3.45 |
| 53 | n-octadecyl | $C_{51}H_{96}O_2N_2 \cdot 2HCl$ | 115-117 | 71.95 | 11.60 | 3.29 | 71.67 | 11.19 | 3.38 |
| 54 | n-octadec-9-enyl | $C_{51}H_{92}O_2N_2 \cdot 2HCl$ | 118-120 | 71.17 | 11.23 | 3.25 | 71.06 | 10.84 | 3.09 |

EXAMPLE 56

1,2-Di-O-(n-hexadecyl)-3-O-(2-[di(2-hydroxyethyl)amino]ethyl)-glycerol Hydrochloride In like manner to that described in Example 11 the named compound was prepared by reacting 1,2-di-O-(n-hexadecyl)-3-O-formylmethyl-glycerol with di(2-hydroxyethyl)amine (solid contained about ¼ mole $H_2O$ per mole named product, m.p. 194°-195° C., elemental analysis calculated: 69.06% C; 12.20% H; 1.96% N; found: 69.12% C; 11.76% H; 1.90% N).

EXAMPLE 57

In Vivo Activity of 1,3-Di-O-(n-hexadecyl)-2-O-(3-aminopropyl)-glycerol Hydrochloride Against EMC Virus Formulation as an emulsion was accomplished by melting and mixing equal parts of the named compound, polysorbate 80, and glycerin, and then dispersing the mixture in hot water under vigorous mixing. The formulation was then adjusted to final concentrations of 0.14 M sodium chloride and 0.01 M sodium phosphate, pH 7. Further dilutions were made with 0.14 M sodium chloride −0.01 M sodium phosphate, pH 7 buffer solution.

Three groups of ten female albino mice (20-25 g. body weight) were given 0.5 ml. intraperitoneal injections containing dosage levels of 1.5, 5 and 15 mg. of the named compound/kg. body weight, respectively. A fourth control group of ten mice was given no such injection. Eighteen to twenty-four hours later all four groups were challenged with 0.2 ml. subcutaneous injection containing 20 times the $LD_{50}$, the dosage level causing a 50% death rate in unprotected mice in ten days, of encephalomyocarditis (EMC) virus. Survival data were recorded over the next ten days and the relative survival ($S_r$) calculated:

| Dosage Level of Named Compound | $S_r$ (average of seven experiments) |
|---|---|
| 15 mg./kg. | 61 |
| 5 | 45 |
| 1.5 | 24 |

Antiviral activity is expressed as the relative survival ($S_r$) in experimental groups compared to the control on the tenth day after challenge. $S_r$ is defined by the formula $$S_r = \left[ \frac{S_x + \sum_{i=1 \text{ to } 10} x_i - \sum_{i=1 \text{ to } 10} e_i}{100 + 100 - \sum_{i=1 \text{ to } 10} e_i} \right] \times 100$$

wherein
- $S_r$ = relative survival
- $S_x$ = percent survival after ten days in experimental group
- $x_i$ = number of survivors on the ith day in experimental group
- $e_i$ = number of survivors on the ith day in control group

EXAMPLES 58-86

In like manner to that described in Example 57 the in vivo activity against EMC virus was determined for the compounds listed below.

| Example Number | Compound Prepared in Example Number | $S_r$ at Dosage Level (mg./kg.) of 15 | 5 | 1.5 | 0.5 |
|---|---|---|---|---|---|
| 58 | 14 | 71 | 49 | 20 | 6 |
| 59 | 15 | 62 | 47 | 18 | — |
| 60 | 16 | 80 | 72 | 20 | — |
| 61 | 17 | 74 | 46 | 4 | — |
| 62 | 18 | 57 | 42 | 3 | — |
| 63 | 19 | 64 | 58 | 15 | — |
| 64 | 20 | 74 | 44 | 34 | — |
| 65 | 21 | 46 | 7 | 6 | — |
| 66 | 22 | 45 | 5 | 4 | — |
| 67 | 23 | 70 | 36 | 3 | — |
| 68 | 24 | 37 | 31 | 12 | 0 |
| 69 | 25 | 44 | 30 | 8 | — |
| 70 | 26 | 68 | 43 | 2 | — |
| 71 | 27 | 66 | 45 | 17 | — |
| 72 | 28 | 68 | 28 | 33 | — |
| 73 | 29 | 60 | 63 | 16 | — |
| 74 | 30 | 53 | 34 | 16 | 7 |
| 75 | 31 | 56 | 35 | 20 | 6 |
| 76 | 32 | 63 | 41 | 31 | — |
| 77 | 42 | 33 | 26 | 26 | — |
| 78 | 43 | 30 | 30 | 7 | — |
| 79 | 44 | 51 | 20 | 7 | — |
| 80 | 46 | 32 | 3 | 0 | — |
| 81 | 47 | 56 | 16 | 6 | — |
| 82 | 51 | 77 | 58 | 26 | — |
| 83 | 52 | 76 | 85 | 42 | — |
| 84 | 53 | 52 | 42 | 32 | — |
| 85 | 54 | 79 | 72 | 28 | — |
| 86 | 49 | 99 | 26 | 54 | — |

EXAMPLE 87

Reduction of Virus Yield on Human Polyp Cells In Vitro by 1,3-Di-O-(n-hexadecyl)-2-O-(3-aminopropyl)-glycerol Hydrochloride Growth medium was prepared by supplementing Eagle's minimum essential medium (100 ml.) with 100× concentrated antibioticantimycotic solution (2 ml.), 200 mM glutamine solution (1 ml.), 100× concentrated nonessential amino acids solution (1 ml.), 100 mM sodium pyruvate solution (1 ml.), and heat-inactivated fetal calf serum (10%). Each well of 96-well microtiter plates was seeded with about 50,000 human nasal polyp cells suspended in 0.2 ml. growth medium. The plates were then incubated for 8-10 days at 37° C. in a 5% $CO_2$ atmosphere to establish monolayers of cells.

At the end of the 8-10 day cell growth period confluent monolayers on the plates were washed four times with phosphate buffered saline and immediately afterward treated with 0.2 ml. per well of maintenance medium containing 10, 5.0, 1.0, 0.5, 0.1 and 0 μg./ml. of the named compound, respectively. The maintenance medium was identical to the growth medium described above except that the level of said fetal calf serum was 2%. The plates were incubated for another 18 hours at 37° C., and the monolayers then washed four times with phosphate buffered saline to remove the named compound, challenged with a composition containing about 1000 times the $TCID_{50}$, i.e. the dosage level causing a 50% infection rate in unprotected cultures, of vesicular stomatitis virus (VSV) for a two hour (37° C.) adsorption period, washed four times with phosphate buffered saline to remove unadsorbed virus particles, and refed with 0.2 ml. per well of said maintenance medium. The plates were then incubated for 7 hours at 37° C., and the culture fluid from 5-8 replicate cells harvested from each plate, stored frozen in test tubes, and then titrated for the amount of infectious virus present in microtiter plates of L-929 mouse fibroblasts. The L-929 mouse cultures were scored microscopically and analyzed about three to four days later, with the following percentage decreases in virus yield (with respect to the control) determined for the five concentrations of named compound tested:

| Percentage Reduction of Virus Yield Concentration (μg./ml.) of Named Compound | | | | |
|---|---|---|---|---|
| 10 | 5.0 | 1.0 | 0.5 | 0.1 |
| 94% | 90% | 84% | 75% | <68% |

EXAMPLES 88-121

In like manner to that described in Example 87 the reduction of virus yield on human polyp cells in vitro was determined for the compounds listed below.

| Example Number | Compound Prepared in Example Number | Percentage Reduction of Virus Yield[a] Concentration (μg./ml.) | | | | |
|---|---|---|---|---|---|---|
| | | 10 | 5.0 | 1.0 | 0.5 | 0.1 |
| 88 | 6 | + | + | − | − | ND |
| 89 | 9 | ND | ± | − | − | ND |
| 90 | 11 | + | + | − | ND | ND |
| 91 | 12 | + | + | − | ND | ND |
| 92 | 13 | + | ± | − | ND | ND |
| 93 | 14 | + | + | − | − | − |
| 94 | 18 | + | − | − | ND | ND |
| 95 | 19 | + | + | − | − | − |
| 96 | 20 | + | ± | − | − | − |
| 97 | 22 | + | ± | − | − | − |
| 98 | 23 | + | ± | − | − | − |
| 99 | 28 | + | + | − | − | − |
| 100 | 30 | + | + | − | ND | ND |
| 101 | 31 | + | + | − | ND | ND |
| 102 | 33 | + | + | − | ND | ND |
| 103 | 34 | ND | + | − | ND | ND |
| 104 | 35 | + | ± | − | ND | ND |
| 105 | 36 | + | − | − | ND | ND |
| 106 | 37 | + | + | − | ND | ND |
| 107 | 38 | + | + | − | − | ND |
| 108 | 40 | + | + | − | ND | ND |
| 109 | 41 | ND | + | − | ND | ND |
| 110 | 42 | + | + | − | − | ND |
| 111 | 44 | + | + | − | ND | ND |
| 112 | 45 | + | − | − | ND | ND |
| 113 | 47 | + | + | − | − | − |
| 114 | 56 | + | − | − | ND | ND |
| 115 | 48 | + | + | − | − | ND |
| 116 | 49 | − | − | − | − | ND |
| 117 | 50 | + | + | − | − | ND |
| 118 | 51 | + | ± | − | − | ND |
| 119 | 52 | + | + | − | − | ND |
| 120 | 53 | + | + | − | − | ND |
| 121 | 54 | + | − | − | − | ND |

[a] + = >68% reduction;
± = ~68% reduction;
− = <68% reduction;
ND = not done.

EXAMPLE 122

Ability of 1,3-Di-O-(n-hexadecyl)-2-O-(3-aminopropyl)-glycerol Hydrochloride to Induce Circulating Interferon A mixture of equal weights of the named compound, polysorbate 80 and glycerol was fused and then homogenized in hot 0.14 M sodium chloride containing 0.01 M sodium phosphate, pH 7 (PBS). The resulting oil-in-water emulsion was readily diluted with PBS for administration.

Female Swiss mice (20–25 g. body weight) were injected (0.5 ml., intraperitoneal) with a quantity of the above diluted emulsion containing 25 mg. of the named compound/kg. body weight. Eight, twelve, sixteen and twenty hours after injection samples of plasma were withdrawn from four mice and pooled. Serial dilutions in L-15 (Leibovitz) medium containing 5% fetal calf serum were incubated in microtiter plates overnight at 37° C. on confluent monolayers of L-929 mouse fibroblasts. The monolayers were then washed with protein-free medium, challenged with 10 times the $TCID_{50}$, i.e. the dosage level causing a 50% infection rate in unprotected cultures, of vesicular stomatitis virus (VSV) for a one hour (37° C.) adsorption period, washed, retreated with L-15 medium containing 5% fetal calf serum and then incubated again for 48 hours at 37° C. The L-929 cultures were then scored microscopically for viral cytopathology and analyzed, with the plasma interferon level, the reciprocal of the plasma dilution conferring 50% protection to the L-929 monolayers, determined.

A second experiment followed the above procedure, except that the mice were injected with 10 mg. of the named compound/kg. body weight and samples of peritoneal wash were taken from four mice and pooled at six, nine, twelve, fifteen and eighteen hours after injection. The samples were taken by exposing the peritoneal membrane, injecting 1 ml. of Hank's balanced salt solution containing 100 penicillin units/ml. and 100 μg. streptomycin/ml. into the peritoneal cavity, briefly massaging the abdomen, and then aspirating the peritoneal wash.

The following data were obtained from these two experiments:

| Source of Interferon | Interferon Levels (units/ml.) Time (hrs.) after Injection | | | | | | | |
|---|---|---|---|---|---|---|---|---|
| | 6 | 8 | 9 | 12 | 15 | 16 | 18 | 20 |
| Plasma | — | 34 | — | 67 | — | 52 | — | 40 |
| Peritoneal wash | <16 | — | 768 | 320 | 448 | — | 448 | — |

EXAMPLES 123–129

In like manner to that described in Example 122 the ability to induce circulating interferon was determined for the compounds listed below.

| Example Number | Compound Prepared in Example Number | Interferon Levels (units/ml.)[a] Time (hrs.) after Injection | | | | Interferon Levels (units/ml.)[b] Time (hrs.) after Injection | | | | |
|---|---|---|---|---|---|---|---|---|---|---|
| | | 8 | 12 | 16 | 20 | 6 | 9 | 12 | 15 | 18 |
| 123 | 14 | <20 | 23 | 75 | 90 | <13 | <13 | 39 | 35 | 72 |
| 124 | 15 | 20 | 71 | 54 | 68 | <18 | <18 | 43 | 59 | 32 |
| 125 | 16 | <18 | 138 | 217 | 163 | <13 | <13 | 43 | 92 | 57 |
| 126 | 24 | <20 | 28 | 60 | 70 | <13 | <13 | 91 | 109 | 50 |
| 127 | 32 | 38 | 33 | 45 | 35 | <13 | 79 | 49 | 52 | <13 |
| 128 | 47 | <17 | 19 | 45 | 99 | <16 | 32 | 96 | 640 | 512 |
| 129 | 51 | 70[c] | 100 | 120[d] | 100[e] | <13 | 109 | 284 | 312 | 224 |

[a] Interferon source - plasma
[b] Interferon source - peritoneal wash
[c] <20 units/ml. at 6 hrs., 70 units/ml. at 9 hrs.
[d] 15 hrs.
[e] 18 hrs.

EXAMPLE 130

Enhancement of Polyinosinic-Polycytidylic Acid [Poly (I:C)]-induced Cellular Resistance to Viral Infection by 1,3-Di-O-(n-hexadecyl)-2-O-(3-aminopropyl)-glycerol Hydrochloride Growth medium was prepared by supplementing Eagle's minimum essential medium (100 ml.) with 100× concentrated antibiotic-antimycotic solution (2 ml.), 200 mM glutamine solution (1 ml.), and heat-inactivated fetal calf serum (5%). Mouse L-929 fibroblasts were suspended in growth medium, and each well of 96-well microtiter plates was seeded with 0.2 ml. of said suspension containing 20,000 to 30,000 cells. The plates were incubated for 2 to 4 days at 37° C. in a 5% $CO_2$ atmosphere to establish monolayers of cells. The plates were washed four times with phosphate buffered saline immediately prior to treatment.

Poly (I:C) was prepared at concentrations of 5.0, 1.0, 0.2 and 0.04 μg./ml. in the medium described above minus calf serum. 0.1 ml. of each dilution was combined in a checkerboard arrangement on the L-929 cell monolayers with 0.1 ml. dilutions containing 20.0, 4.0, 0.8, 0.16 and 0.032 μg. of the named compound per ml. said serum-free medium. Control wells were exposed to either poly(I:C) or the named compound alone. The plates were incubated for 6 hours at 37° C. in a 5% $CO_2$ atmosphere, washed four times with phosphate buffered saline, and refed with 0.1 ml. per well growth medium containing 2% fetal calf serum. After 18 more hours of incubation, the plates were scored for toxicity and then challenged with 0.1 ml. per well of a vesicular stomatitis virus (VSV) suspension containing 10 to 30 times the $TCID_{50}$ (tissue culture infective dose causing a 50% infection rate). The plates were incubated for another 3 to 4 days and then scored microscopically for cytopathogenic effect (CPE). Cells protected from virus infection were free of CPE. The minimum protective dose (MPD) of poly (I:C) alone was noted, and the amount of enhanced or augmented antiviral activity caused by combination with the named compound recorded for each dilution level of said named compound.

| Enhancement of Poly (I:C)-induced Cellular Resistance to Viral Infection Concentration (μg./ml.) of Named Compound | | | | |
|---|---|---|---|---|
| 20.0 | 4.0 | 0.8 | 0.16 | 0.032 |
| 125X | 125X | 125X | 5X | <5X |

Note: combining poly(I:C) with named compound provides some antiviral effect as increasing poly (I:C) concentration indicated number of times.

EXAMPLES 131–162

In like manner to that described in Example 130 the enhancement of poly(I:C)-induced cellular resistance to viral infection was determined for the compounds listed below.

| Example Number | Compound Prepared in Example Number | Poly (I:C) Enhancement[a] Concentration (μg./ml.) | | |
|---|---|---|---|---|
| | | 20 | 4.0 | 0.8 |
| 131 | 6 | + | + | − |
| 132 | 7 | + | + | − |
| 133 | 14 | + | + | ± |
| 134 | 15 | + | + | ± |
| 135 | 16 | + | + | ± |
| 136 | 17 | + | + | ± |
| 137 | 18 | + | + | ± |
| 138 | 19 | + | + | ± |
| 139 | 20 | + | + | ± |
| 140 | 21 | + | ± | − |
| 141 | 22 | − | − | − |
| 142 | 23 | + | + | ± |
| 143 | 24 | + | + | ± |
| 144 | 25 | + | + | − |
| 145 | 26 | + | − | − |
| 146 | 27 | + | + | − |
| 147 | 28 | + | + | − |
| 148 | 29 | + | + | − |
| 149 | 30 | + | + | ± |
| 150 | 31 | + | + | − |
| 151 | 32 | + | + | ± |
| 152 | 40 | + | + | ± |
| 153 | 41 | + | + | − |
| 154 | 42 | + | + | + |
| 155 | 43 | + | + | + |
| 156 | 44 | + | + | ± |
| 157 | 46 | + | + | ± |
| 158 | 47 | + | + | ± |
| 159 | 51 | + | + | ± |
| 160 | 52 | + | + | − |
| 161 | 53 | + | + | ± |
| 162 | 54 | ± | − | − |

[a] + = >5X enhancement;
± = ~5X enhancement;
− = <5X enhancement;
ND = not done.

What is claimed is:

1. A compound selected from those of the formula

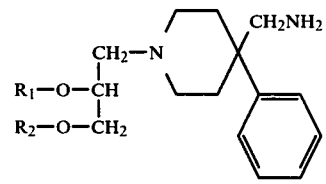

and the pharmaceutically acceptable acid addition salts thereof, wherein $R_1$ and $R_2$ are each selected from the group consisting of normal alkyl of from 12 to 20 carbon atoms and normal alkenyl not having a double bond in the 1-position of from 12 to 20 carbon atoms.

2. A compound of claim 1 wherein $R_1$ and $R_2$ are each normal alkyl of from 14 to 18 carbon atoms.

3. A compound of claim 2 wherein $R_1$ and $R_2$ each contain the same number of carbon atoms.

4. The compound of claim 1 wherein $R_1$ and $R_2$ are each n-tetradecyl.

5. The compound of claim 1 wherein $R_1$ and $R_2$ are each n-hexadecyl.

6. The compound of claim 1 wherein $R_1$ and $R_2$ are each n-octadecyl.

7. A pharmaceutical composition containing an antivirally effective amount of a compound of claim 1 as the essential active ingredient in a pharmaceutically acceptable carrier.

8. A method of prophylactically controlling a viral infection in a mammal which comprises administering an amount effective to prophylactically control said viral infection of a compound of claim 1.

9. A method of inducing the production of interferon in a mammal which comprises administering an amount effective to induce the production of interferon of a compound of claim 1.

* * * * *